United States Patent
Haining et al.

(10) Patent No.: US 10,653,123 B2
(45) Date of Patent: May 19, 2020

(54) METHODS AND COMPOSITIONS FOR PERTURBING GENE EXPRESSION IN HEMATOPOIETIC STEM CELL LINEAGES IN VIVO

(71) Applicants: Dana-Farber Cancer Institute, Inc., Boston, MA (US); President and Fellows of Harvard College, Cambridge, MA (US)

(72) Inventors: William N. Haining, Newton, MA (US); Arlene H. Sharpe, Brookline, MA (US); Jernej Godec, Brookline, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 162 days.

(21) Appl. No.: 15/314,251

(22) PCT Filed: May 27, 2015

(86) PCT No.: PCT/US2015/032573
§ 371 (c)(1),
(2) Date: Nov. 28, 2016

(87) PCT Pub. No.: WO2015/183885
PCT Pub. Date: Dec. 3, 2015

(65) Prior Publication Data
US 2017/0215392 A1    Aug. 3, 2017

Related U.S. Application Data

(60) Provisional application No. 62/003,185, filed on May 27, 2014.

(51) Int. Cl.

| | | |
|---|---|---|
| A01K 67/027 | (2006.01) | |
| A61K 35/28 | (2015.01) | |
| A61K 49/00 | (2006.01) | |
| C12N 5/0781 | (2010.01) | |
| C12N 5/0783 | (2010.01) | |
| C12N 15/11 | (2006.01) | |
| C12N 15/86 | (2006.01) | |
| G01N 33/50 | (2006.01) | |

(52) U.S. Cl.
CPC .......... *A01K 67/0271* (2013.01); *A61K 35/28* (2013.01); *A61K 49/0008* (2013.01); *C12N 5/0635* (2013.01); *C12N 5/0636* (2013.01); *C12N 15/11* (2013.01); *C12N 15/86* (2013.01); *G01N 33/505* (2013.01); *G01N 33/5052* (2013.01); *G01N 33/5088* (2013.01); *A01K 2207/12* (2013.01); *A01K 2227/105* (2013.01); *A01K 2267/025* (2013.01); *C12N 2310/11* (2013.01); *C12N 2310/14* (2013.01); *C12N 2310/141* (2013.01); *C12N 2310/531* (2013.01); *C12N 2740/15041* (2013.01); *C12N 2740/15043* (2013.01); *C12N 2840/002* (2013.01)

(58) Field of Classification Search
CPC .................................................. A01K 67/0271
See application file for complete search history.

(56) References Cited

FOREIGN PATENT DOCUMENTS

| WO | WO-2001/034843 | 5/2001 | |
|---|---|---|---|
| WO | WO2015/148860 | * 10/2015 | ........... C12N 15/113 |

OTHER PUBLICATIONS

Cronin et al. (Genes & Development. 2001; 15:1506-1517). (Year: 2001).*
Chen et al (Stem Cells. 2000; 18: 352-359). (Year: 2000).*
Mull et al. (Stem Cell Research (2014) 12, 539-549). (Year: 2014).*
Bettini et al., "T-cell receptor retrogenic mice: a rapid, flexible alternative to T-cell receptor transgenic mice," Immunology, 136(6): 265-272 (2012).
Chen et al., "Lentiviral vector transduction of hematopoietic stem cells that mediate; long-term reconstitution of lethally irradiated mice," Stem Cells, Stem Cells 18(5): 352-359 (2000).
McCune et al., "The SCID-hu mouse: Murine model for the analysis of human hematolymphoid differentiation and function," Science, 241:1632-1639 (1988).
International Search Report dated Sep. 11, 2015 from PCT/US2015/032573.
Zhou et al., "In vivo discovery of immunotherapy targets in the tumor microenvironment," Nature, 506(7486): 52-57 (2014).

* cited by examiner

*Primary Examiner* — Scott Long
(74) *Attorney, Agent, or Firm* — Foley Hoag LLP

(57) ABSTRACT

The invention provides methods and compositions for perturbing gene expression in hematopoietic cell lineages in vivo.

18 Claims, 11 Drawing Sheets
Specification includes a Sequence Listing.

A

B

C

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: /note="Description of Artificial Sequence:
      sh-Batf shRNA target sequence"

<400> SEQUENCE: 1
ccgcaaagag atcaaacagc t                                              21

<210> SEQ ID NO 2
<211> LENGTH: 21
<212> TYPE: DNA
<213> ORGANISM: Artificial Sequence
<220> FEATURE:
<223> OTHER INFORMATION: /note="Description of Artificial Sequence:
      sh-Batf shRNA target sequence"

<400> SEQUENCE: 2
ctggacaagt attgaacaca a                                              21

<210> SEQ ID NO 3
<211> LENGTH: 21
<212> TYPE: DNA
<213> ORGANISM: Artificial Sequence
<220> FEATURE:
<223> OTHER INFORMATION: /note="Description of Artificial Sequence:
      sh-Batf shRNA target sequence"

<400> SEQUENCE: 3
gagctcaagt acttcacatc a                                              21

<210> SEQ ID NO 4
<211> LENGTH: 21
<212> TYPE: DNA
<213> ORGANISM: Artificial Sequence
<220> FEATURE:
<223> OTHER INFORMATION: /note="Description of Artificial Sequence:
      sh-RFP shRNA target sequence"
```

-continued

```
<400> SEQUENCE: 4
ccgtcatagc gataacgagt t                                              21

<210> SEQ ID NO 5
<211> LENGTH: 21
<212> TYPE: DNA
<213> ORGANISM: Artificial Sequence
<220> FEATURE:
<223> OTHER INFORMATION: /note="Description of Artificial Sequence:
      sh-RFP shRNA target sequence"

<400> SEQUENCE: 5
gcttcaagtg ggagcgcgtg a                                              21

<210> SEQ ID NO 6
<211> LENGTH: 21
<212> TYPE: DNA
<213> ORGANISM: Artificial Sequence
<220> FEATURE:
<223> OTHER INFORMATION: /note="Description of Artificial Sequence:
      sh-GFP shRNA target sequence"

<400> SEQUENCE: 6
acaacagcca caacgtctat a                                              21
```

METHODS AND COMPOSITIONS FOR PERTURBING GENE EXPRESSION IN HEMATOPOIETIC STEM CELL LINEAGES IN VIVO

CROSS-REFERENCE TO RELATED APPLICATIONS

This application claims the benefit of U.S. Provisional Application No. 62/003,185, filed on 27 May 2014; the entire contents of said application are incorporated herein in their entirety by this reference.

STATEMENT OF RIGHTS

This invention was made with government support under grant numbers RO1 AI091493, AI057266, and AI082630 awarded by The National Institutes of Health. The government has certain rights in the invention.

BACKGROUND OF THE INVENTION

Following activation by antigen, co-stimulation and inflammation, naive $CD8^+$ T cells initiate a differentiation program resulting in massive changes in gene expression and cell function, which leads to the formation of effector and memory T cells (Doering et al. (2012) *Immunity* 37:1130-1144). This differentiation program is critical for the development of effective tumor immunity (Galon et al. (2006) *Science* 313:1960-1964) and the control of pathogens (Wong and Pamer (2003) *Annu. Rev. Immunol.* 21:29-70). However, the developing effector $CD8^+$ T cells population is strikingly heterogeneous (Arsenio et al. (2014) *Nat. Immunol.* 15:365-372), and several phenotypically distinct subpopulations of T cells exist within the effector pool that have different lineage potential and function (Joshi et al. (2007) *Immunity* 27:281-295; Sarkar et al. (2008) *J. Exp. Med.* 205:625-640). Thus, $CD8^+$ effector T cells face complex lineage choices during differentiation.

Although the development of effector $CD8^+$ T cells occurs over a period of days (Kaech et al. (2002) (*Cell* 111:837-851), early events in the life-history of T cells are critical in determining the fate of T cells (Kaech and Ahmed (2001) *Nat. Immunol.* 2:415-422; Mercado et al. (2000) *J. Immunol.* 165:6833-6839; van Stipdonk et al. (2001) *Nat. Immunol.* 2:423-429; van Stipdonk et al. (2003) *Nat. Immunol.* 4:361-365; Wong and Pamer (2001) *J. Immunol.* 166:5864-5868). For instance, asymmetric segregation of cell contents during the first cell division after encounter with antigen can profoundly influence the ultimate differentiation state of effector cells (Chang et al. (20017) *Science* 315:1687-1691), suggesting that investigating the events that occur in the hours following antigen encounter will be essential to define the mechanisms that regulate the fate of effector $CD8^+$ T cells.

Effector differentiation is regulated by a set of transcription factors (TFs) including T-bet (Intlekofer et al. (20015) *Nat. Immunol.* 6:1236-1244), Eomes (Pearce et al. (2003) *Science* 302:1041-1043), Blimp1 (Rutishauser et al. (2009) *Immunity* 31:296-308; Shin et al. (2009) *Immunity* 31:309-320), Id2 (Cannarile et al. (2006) *Nat. Immunol.* 7:1317-1325), and Runx3 (Cruz-Guilloty et al. (2009) *J. Exp. Med.* 206:51-59). It has recently been shown that the AP-1 family TF, BATF, is absolutely required for effector $CD8^+$ T cell differentiation and coordinates the program of gene expression essential for this process (Kurachi et al. (2014) *Nat. Immunol.* 15:373-383). Thus, many TFs that are expressed immediately after stimulation may play a role in specifying the fate of developing effector cells from the earliest point in differentiation.

The role of specific TFs in regulating $CD8^+$ T cell effector differentiation has been investigated using germline or conditional KOs. However, these approaches are limited to studying a small number of candidate genes (Kaech and Cui (2012) *Nat. Rev. Immunol.* 12:749-761). In contrast, perturbing genes with RNAi could in principle permit many more candidate regulators to be studied in parallel (Amit et al. (2009) *Science* 326:257-263). However, techniques to deliver shRNAs to T cells are limited by the need to stimulate cells to divide using TCR cross-linking (Yang et al. (2012). *J. Exp. Med.* 209:1655-1670), infection (Joshi et al. (2007) *Immunity* 27:281-295; Araki et al. (2009) *Nature* 460:108-112), or cytokine stimulation (Zhou et al. (2014) *Nature* 506:52-57) in order to achieve meaningful frequencies of transduction with viral vectors encoding shRNA constructs. This strategy of activating T cells in order to deliver shRNAs raises a concern that this activation could profoundly alter the cell at a critical phase of time when even subtle perturbations of TFs can profoundly influence T cell fate (Chang et al. (2007) *Science* 315:1687-1691).

Thus, new approaches, compositions, methods, and systems are required to perturb gene expression in many cell types, including immune and hematopoietic cell types, in a manner that preserves natural cellular differentiation.

SUMMARY OF THE INVENTION

The present invention provides compositions, methods, and systems for overcomes the long-felt difficulties in preserving natural cellular differentiation of cell types while allowing for perturbation of gene expression in such cell types through transduction of desired cell types (e.g., hematopoietic stem cells) with a viral vector that genomically integrates a gene expression perturbation construct of interest to be activated at the desired state of differentiation.

In one aspect, a method of generating transduced resting cells of the hematopoietic stem cell lineage that are differentiated in vivo, comprising: a) obtaining cells of the hematopoietic stem cell lineage; b) transducing the cells with at least one viral vector, wherein each viral vector integrates an exogenous nucleic acid into the genome of the cell; c) transplanting the transduced cells to an immunocompromised incubator animal, wherein the transplanted transduced cells reconstitute the immunocompromised incubator animal immune system; and d) selecting populations of resting reconstituted immune cells of interest from the incubator animal, thereby generating transduced resting cells of the hematopoietic stem cell lineage that are differentiated in vivo, are provided.

Numerous embodiments are contemplated and described herein. For example, in one embodiment, the cells of the hematopoietic stem cell lineage are murine or human. In another embodiment, the cells of the hematopoietic stem cell lineage are selected from the group consisting of hematopoietic stem cells (HSC), common myeloid progenitor cells (CMP), common lymphoid progenitor cells (CLP), committed lymphoid progenitor cells, granulocyte/macrophage progenitor cells (GMP), megakaryocyte/erythroid progenitor cells (MEP), granulocyte progenitor cells, macrophage progenitor cells, erythroid progenitor cells, megakaryocyte progenitor cells (MKP), NK cell progenitor cells (NKP), B cell progenitor cells (BCP), and T cell progenitor cells (TCP). In still another embodiment, the cells of the hematopoietic stem cell lineage are not terminally differentiated or post-mitotic. In yet another embodiment, the cells of the hematopoietic stem cell lineage are not thymocytes or are not derived from the thymus. In another embodiment, the cells of the hematopoietic stem cells lineage are obtained from a biological source selected from the group consisting of bone marrow, umbilical cord blood, amniotic fluid, peripheral blood, and fetal liver. In still another embodiment, the cells are transduced with a single viral vector. In yet another embodiment, the viral vector is a lentiviral vector. In another embodiment, the viral vector inducibly expresses an RNA encoded by the exogenous nucleic acid. In still another embodiment, the inducible expression is regulated using lactose operon operator (LacO) and lactose operon repressor (LacI) sequences. In yet another embodiment, the exogenous nucleic acid is selected from the group consisting of mRNA, antisense RNA, shRNA, siRNA, microRNA, PiwiRNA, and combinations thereof. In another embodiment, the exogenous nucleic acid is an shRNA.

In still other embodiments, the exogenous nucleic acid comprises a) an engineered, non-naturally occurring Clustered Regularly Interspaced Short Palindromic Repeats (CRISPR) guide RNA that hybridizes with a target nucleic acid sequence of interest and/or b) a nucleotide sequence encoding a Type-II Cas9 protein, optionally wherein the cells are transgenic for Cas9. In yet another embodiment, the viral vector further comprises a nucleic acid encoding a reporter, such as a fluorescent protein. In another embodiment, the incubator animal is immunocompromised using lethal irradiation or chemotherapy. In still another embodiment, the incubator animal is immunodeficient. In yet another embodiment, the immunocompromised incubator animal and the animal from which the cells of step a) were obtained are congenic. In another embodiment, transplantation of the transduced cells to the innmunocompromised incubator animal is autologous, syngeneic, allogeneic, or xenogeneic.

In still other embodiments, the resting reconstituted immune cells of interest selected in step d) are selected from the group consisting of terminally differentiated cells, post-mitotic cells, and/or unactivated cells. In yet another embodiment, the resting reconstituted immune cells of interest selected in step d) have not been exogenously stimulated to divide. In another embodiment, the resting reconstituted immune cells of interest selected in step d) are resting T cells or resting B cells. In still another embodiment, the resting reconstituted immune cells of interest selected in step d) are isolated. In yet another embodiment, any method described herein further comprises a step e) of culturing the selected cells in vitro and monitoring the selected cells in response to exogenous perturbation. In another embodiment, any method described herein further comprises a step c) of transplanting the transduced resting cells of the hematopoietic stem cell lineage that are differentiated in vivo into an experimental animal and monitoring the transplanted cells in response to exogenous perturbation. In still another embodiment, the exogenous perturbation is the application of an assay for testing autoimmune, allergic, vaccination, immunotolerance, cancer immunotherapy, immune exhaustion, immunological memory, immunological epitope, stem cell, hematopoietic stem cell, or immune disease responses.

In another aspect, transduced resting cells of the hematopoietic stem cell lineage that are differentiated in vivo produced according to any method described herein, are provided.

In still another aspect, non-human animals comprising transduced resting cells of the hematopoietic stem cell lineage that are differentiated in vivo produced according to any method described herein, are provided.

Figure 1:
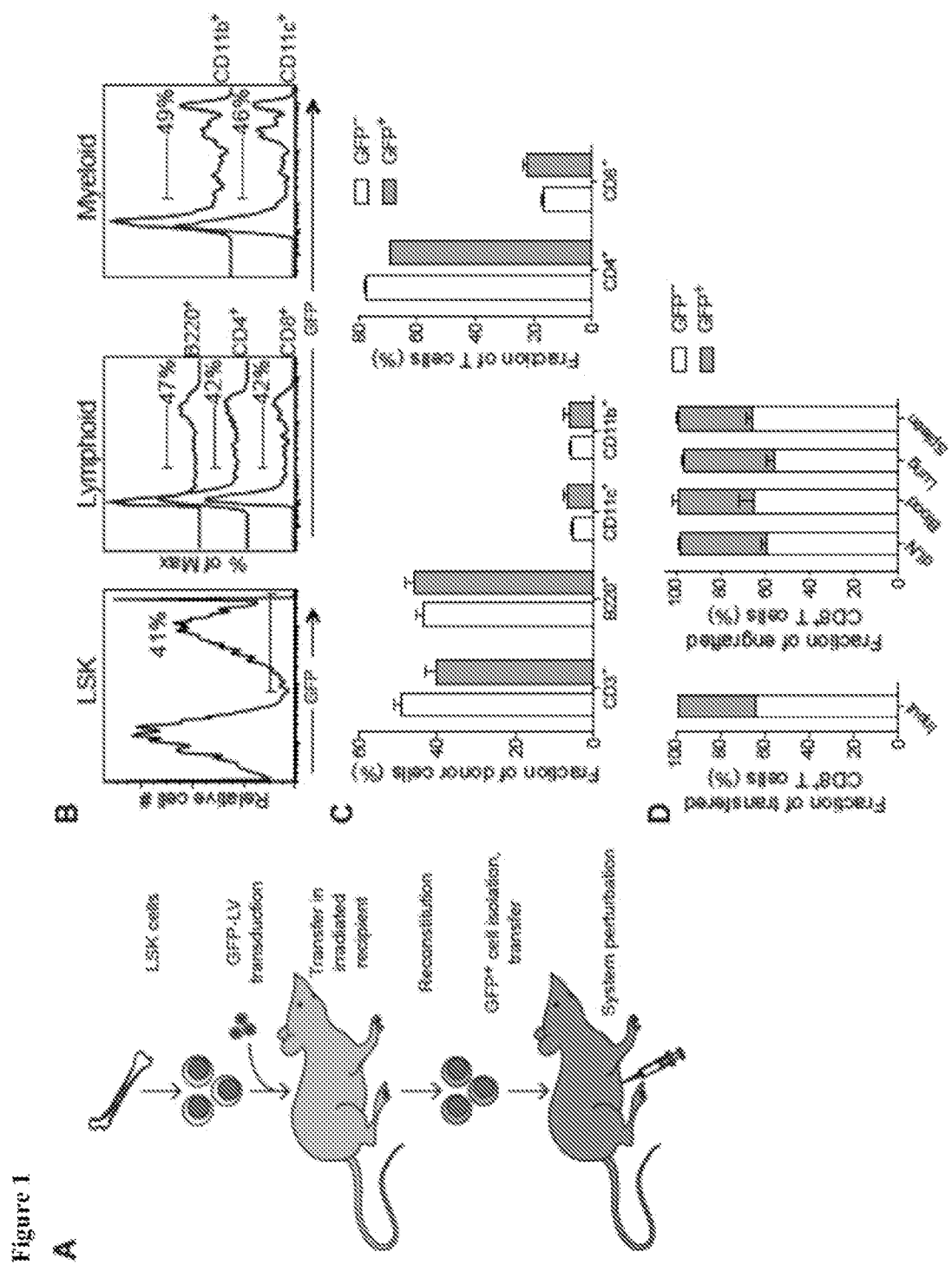
FIG. 1 includes 4 panels, identified as panels A, B, C, and D, which show that transduced bone marrow progenitor populations efficiently reconstitute myeloid and lymphoid compartments and develop normally into functional CD8$^+$ T cells. Panel A shows a schematic diagram of transduction strategy. Panel B shows the fraction of LSK cells (left panel) transduced with GFP-expressing lentivirus at the time of transplant, and in lymphoid (middle panel) and myeloid (right panel) cell populations following engraftment. Panel C shows the fraction of transduced (GFP$^+$) and untransduced (GFP$^-$), donor-derived cells in immune lineages indicated following engraftment. Panel D shows the fraction of transduced (GFP$^+$) and untransduced (GFP$^-$), donor-derived cells naive P14 CD8$^+$ T cells (left panel) prior to adoptive transfer, and of effector (right panel) P14 CD8$^+$ T cells in tissues indicated 10 days following transfer and subsequent host infection with PR8-GP33 influenza.

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

Modulating gene expression (e.g., increasing gene expression using recombinant nucleic acids or inhibiting gene expression using shRNA constructs and other modes of RNA interference) may reveal critical regulators of biological processes in the immune system and also provide a basis upon which to prioritize molecules for therapeutic development. However, there are numerous limitations of current techniques to modulate gene expression in immune system cells using exogenous vectors. For example, retroviruses like lentiviruses may transduce some types of nonproliferating cells, but have marked difficulty in transducing many important immune cell types, such as resting T and B cells. Although transduction in such refractory immune cell types may be forced by various techniques, such as cellular activation via the T-cell receptor (TCR), exposure to activating cytokines, electroporation, nanowire delivery, and the like, such techniques significantly perturb the cell state and induce surface receptors and differentiation programs that limit the interpretation of cell function in gene expression modulation experiments (see, for example, Verhoeycn et al. (2009) *Mehods Mol. Biol.* 506:97-114 and Frecha et al. (2008) *Blood* 112:4843-4852). Moreover, it is increasingly becoming appreciated that complex immunological interactions, such as interactions of T cells with tumors are most accurately modeled in vivo and the requirement to transduce T cells in vitro puts such assays beyond reach.

By contrast, the present invention is based in part on the discovery of methods allowing for the modulation of gene expression in numerous immune cell types that have heretofore been refractory to transduction in a manner that preserves the in vivo state of the immune cell based upon the transduction of parent cell types with genetic constructs of interest followed by in vivo development, selection, and/or isolation of the transduced cells. The present invention further provides transduced cells resulting from such methods, as well as non-human animals comprising such transduced cells. Moreover, the present invention provides methods of using such cells and non-human animals for numerous applications including, but not limited to, assays useful for testing autoimmune, allergic, vaccination, immunotolerance, cancer immunotherapy, immune exhaustion, immunological memory, immunological epitope, stem cell, hematopoietic stem cell, or immune disease responses to gene expression perturbation.

The present invention overcomes numerous, sequential technical unsolved challenges in the art. For example, cellular transduction conditions were determined to generate transduction frequencies sufficiently high as to make the process feasible, but low enough to avoid multiple integrations per cell which would be problematic for the use of the technology for pooled screens. In addition, it was not expected that transplantation of lentivirally transduced cells would result in efficient the engraftment of modified hematopoietic cells with similar frequencies to unmodified HSCs. Similarly, the function of naive cells arising from transduced HSCs (e.g., T cells), either due to the presence of integrated lentivirus or as a result of the transplantation process resulting in homeostatic proliferation, may have been compromised. However, the methods described herein generate naive cells (e.g., T cells) from transduced FISCs having phenotypes indistinguishable from those of wild-type naive cells (e.g., T cells). It was further determined that such cells were capable of differentiating into fully functional cells (e.g., effector CD8 T cells). It was also confirmed that IPTG dosing and administration conditions could be used to generate efficient gene knockdown in primary cells (e.g., T and B cells) since whether IPTG dose and administration strategies to achieve gene knockdown in primary cells of hematopoietic origin were unknown. Moreover, initial experiments revealed that HSCs transduced with lentiviral vectors expressing Thy1 as a marker of transduction did not persist following transplantation, indicating that markers other than Thy1, such as GFP, were required to be used as a marker of transduction allowed efficient engraftment. Finally, during the 6-8 week period following transplantation of modified HSCs, extensive differentiation, proliferation, and migration results in the generation of naive cells (e.g., T cells) from the parental HSCs. It was not heretofore known what number of transduced progenitors gives rise to the naive pool. For example, if the naive T cell pool was generated from a small number of progenitors, then the number of different vectors that could be delivered to the naive T cell pool would be small. However, it has been determined herein that at least 100 different vectors could be transmitted from the progenitor pool to naive CD8 T cells and then to effector CD8 T cells.

A. Hematopoietic Stem Cell Lineages and Cell Sources for Transduction

The methods and compositions described herein use cells of the hematopoietic stem cell (HSC) lineage for transduction purposes. Various cell types in the HSC lineage, as well as methods for selecting, purifying, and isolating such cell types, are well known in the art (see, for example, U.S. Pat.

No. 8,481,315). Cell types of interest may be obtained from any animal having an immune system. In one embodiment, cell types of interest are obtained from a mammal, including humans. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). For example, cell types of interest having a defined genetic background or unknown genetic background may be obtained from a human for use in the methods of the present invention. In one embodiment, cells having a defined T Cell receptor are useful for analysis since all progeny will be specific for a limited range of specific peptides. For example, TCRalpha knockout/transgenic LCMV P14 TCR transgenic mice does not develop endogenous mature TCR alpha beta cells and whose peripheral T cells are almost all CD8+ and express transgenic TCR specific for a peptide (P14) from the lymphocytic choriomeningitis virus (LCMV) presented by the MHC class I molecule H-2Db (see, for example, Bettini et al. (2012) *Immunol.* 136:265-272). In another embodiment, cell types of interest may be obtained from non-human mammals. Representative, non-limiting examples of non-human mammals include non-human primates (e.g., monkeys and chimpanzees), rodents (e.g., rats, mice, and guinea pigs), canines, felines, birds, fish, and ruminants (e.g., cows, sheep, pigs, and horses). In still another embodiment, the non-human mammal is a mouse. The animals from which cell types of interest are obtained may be adult, newborn (e.g., less than 48 hours old), immature, or in utero. Cell types of interest may be primary cells, stem cells, and zygotes. In yet another embodiment, human progenitor cells are used to reconstitute human immune systems in host animals such as mice. Such systems are well known in the art and include, for example, SCID:Hu models in which human cells are reconstituted in SCID mice (see, for example, McCune et al. (1988) *Science* 241:1632-1639).

As used herein, "obtained" from a biological material source means any conventional method of harvesting or partitioning a source of biological material from a donor. For example, biological material may obtained from a blood sample, such as a peripheral or cord blood sample, or harvested from bone marrow or amniotic fluid. Methods for obtaining such samples are well known to the artisan. In the present invention, the samples may be fresh (i.e., obtained from a donor without freezing). Moreover, the samples may be further manipulated to remove extraneous or unwanted components prior to expansion. The samples may also be obtained from a preserved stock. For example, in the case of peripheral or cord blood, the samples may be withdrawn from a cryogenically or otherwise preserved bank of such blood. Such samples may be obtained from any suitable donor.

"Hematopoictic stem cells" or "HSC" are clonogenic, self-renewing pluripotent cells capable of ultimately differentiating into all cell types of the Hematopoictic system, including B cells T cells, NK cells, lymphoid dendritic cells, myeloid dendritic cells, granulocytes, macrophages, megakaryocytes, and erythroid cells. HSC self-renewal refers to the ability of an HSC cell to divide and produce at least one daughter cell with the same self-renewal and differentiation potential of a HSC; that is, cell division gives rise to additional HSCs. Self-renewal provides a continual source of undifferentiated stem cells for replenishment of the hematopoietic system. Several sub-types of HSC are known. For example, "short term repopulating hematopoietic stem cells" or "ST-HSC" refers to HSC that have limited, short term self-renewing capacity, and are characterized by their capacity to differentiate into cells of the myeloid and lymphoid lineage. ST-HSC are distinguished from long-term repopulating (LT) HSC by their limited length of self-renewal activity in culture assays (e.g., approximately 8 weeks, see, for example, Christensen and Weissman (2001) *Proc. Natl. Acad. Sci. USA*. 98:14541-14546).

"Self-renewal" refers to the ability of a cell to divide and generate at least one daughter cell with the identical (e.g., self-renewing) characteristics of the parent cell. The second daughter cell may commit to a particular differentiation pathway. For example, a self-renewing hematopoietic stem cell divides and forms one daughter stem cell and another daughter cell committed to differentiation in the myeloid or lymphoid pathway. A committed progenitor cell has typically lost the self-renewal capacity, and upon cell division produces two daughter cells that display a more differentiated (i.e., restricted) phenotype.

In some embodiments, "HSC lineage cells" may refer to any cell type, stage of development, marker expression state, and the like of a cell that may be naturally obtained from an HSC. In other embodiments, HSC lineage cells are limited to cells of the hematopoietic stem cell lineage that are not terminally differentiated, post-mitotic, thymocytes, derived from the thymus, and/or otherwise functional.

As with other cells of the hematopoietic system, HSCs are typically defined by the presence of a characteristic set of cell markers. "Enriched" when used in the context of HSC refers to a cell population selected based on the presence of a single cell marker, generally CD34+, while "purified" in the context of HSC refers to a cell population resulting from a selection on the basis of two or more markers, such as CD34+ and CD90+.

"Marker phenotyping" refers to identification of markers or antigens on cells for determining their phenotype (e.g., differentiation state and/or cell type). This may be done by immunophenotyping, which uses antibodies that recognize antigens present on a cell. The antibodies may be monoclonal or polyclonal, but are generally chosen to have minimal cross reactivity with other cell markers. It is to be understood that certain cell differentiation or cell surface markers are unique to the animal species from which the cells are derived, while other cell markers will be common between species. These markers defining equivalent cell types between species are given the same marker identification even though there are species differences in structure (e.g., amino acid sequence). Cell markers include cell surfaces molecules, also referred to in certain situations as cell differentiation (CD) markers, and gene expression markers. The gene expression markers are those sets of expressed genes indicative of the cell type or differentiation state. In part, the gene expression profile will reflect the cell surface markers, although they may include non-cell surface molecules.

As used herein, "enriched" means that the percentage of marker phenotyped cells relative to other cells in a population is increased. In one embodiment, "purified" means that the percentage of marker phenotyped cells is substantially pure and excludes cells that are not marker phenotyped. A "substantially pure cell population" refers to a population of cells having a specified cell marker characteristic and differentiation potential that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or more, or any value or range in between, of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

In one embodiment, "isolated" refers to a product, compound, or composition which is separated from at least one other product, compound, or composition with which it is associated in its naturally occurring state, whether in nature or as made synthetically. In other embodiments, "isolated" means that desired marker phenotyped cells are physically separated from other cell populations. Methods for the enrichment, purification, and/or isolation of marker phenotyped cells are disclosed herein and are also well known in the art, such as by using fluorescence-activated cell scanning (FACS), magnetic cell sorting, and centrifugation (see, for example, U.S. Pat. Nos. 5,474,687, 5,677,136, and 6,004,743; and U.S. Pat. Publ. 2001/0039052).

The marker phenotypes useful for identifying HSC are well known in the art. For human HSC, for example, the cell marker phenotypes preferably include CD34$^+$ CD38$^-$ CD90 (Thy1)$^+$ Lin$^-$. For mouse HSCs, an exemplary cell marker phenotype is Sca-1$^+$ CD90$^+$ (see, e.g., Spangrude et al. (1988) Science 1:661-673) or c-kit$^+$ Thy$^{lo}$ Lin$^-$ Sca-1$^+$ (see, Uchida et al (1990). J. Clin. Invest. 101:961-966). Alternative HSC markers such as aldehyde dehydrogenase and AC133 may also be used (see, for example, Storms et al. (1999) Proc. Natl. Acad. Sci. U.S.A. 96:9118-9123 and Yin et al. (1997) Blood 90:5002-5012).

As stated above, HSC are clonogenic cells, which possess the properties of both self-renewal (expansion) and multi-lineage potential giving rise to all types of mature blood cells. HSC are responsible for hematopoiesis and undergo proliferation and differentiation to produce mature blood cells of various lineages while still maintaining their capacity for self-renewal. The ability to self-renew maintains the HSC population for the lifespan of an animal and also allows HSC to repopulate the bone marrow of lethally irradiated hosts. Early HSC development displays a hierarchical arrangement, starting from long-term (LT-) HSCs, which have extensive self-renewal capability, followed by the expansion state, which corresponds to short-term (ST-) HSCs (having limited self-renewal ability) and proliferative multipotent progenitors (MPP) (having multipotent potential but no self-renewal capability). MPP is also a stage of priming or preparation for differentiation. An MPP differentiates and, during this process, the more primitive population gives rise to a less primitive population of cells, which is unable to give rise to a more primitive population of cells. Genetic programs control these processes, including the multipotential, self-renewal, and activation (or transient amplification) of HSCs, and lineage commitment from MPP to lymphoid and myeloid progenitor cells.

Thus, HSCs give rise to committed lymphoid or myeloid progenitor cells. "Committed myeloid progenitor cells" refer to cell populations capable of differentiating into any of the terminally differentiated cells of the myeloid lineage. Encompassed within the myeloid progenitor cells are the "common myeloid progenitor cells (CMP)", a cell population characterized by limited or non-self-renewal capacity but which is capable of cell division to form granulocyte/macrophage progenitor cells (GMP) and megakaryocyte/erythroid progenitor cells (MEP). Such cell populations may then give rise to myeloid dendritic, myeloid erythroid, erythroid, megakaryocytes, granulocyte/macrophage, granulocyte, and macrophage cells. Non-self-renewing cells refers to cells that undergo cell division to produce daughter cells, neither of which have the differentiation potential of the parent cell type, but instead generates differentiated daughter cells. Committed progenitor cells of the myeloid lineage include oligopotent CMP, GMP, and MEP as defined herein, but also encompass unipotent erythroid progenitor, megakaryocyte progenitor, granulocyte progenitor, and macrophage progenitor cells. Different cell populations of myeloid progenitor cells are distinguishable from other cells by their differentiation potential, and the presence of a characteristic set of cell markers. The marker phenotypes useful for identifying CMPs include those well known in the art. For CMP cells of murine origin, for example, the cell population is characterized by the marker phenotype c-Kit$^{high}$ (CD117) CD16$^{low}$ CD34$^{low}$ Sca-1$^{neg}$ Lin$^{neg}$ and further characterized by the marker phenotypes FcγR$^{lo}$ IL-7Rα$^{neg}$ (CD127). The murine CMP cell population is also characterized by the absence of expression of markers that include B220, CD4, CD8, CD3, Ter119, Gr-1 and Mac-1. For CMP cells of human origin, the cell population is characterized by CD34$^+$ CD38$^+$ and further characterized by the marker phenotype, CD123$^+$ (IL-3Rα) CD45RA$^{neg}$. The human CMP cell population is also characterized by the absence of cell markers CD3, CD4. CD7, CD8, CD10, CD11b, CD14, CD19, CD20, CD56, and CD234a. Descriptions of marker phenotypes for various myeloid progenitor cells are described in, for example, U.S. Pat. Nos. 6,465,247 and 6,761,883 and Akashi (2000) Nature 404:193-197.

A committed progenitor cell of the myeloid lineage is the "granulocyte/macrophage progenitor cell (GMP)". GMP are cells derived from common myeloid progenitor cells, and characterized by a capacity to give rise to granulocyte (e.g., basophils, eosinophils, and neutrophils) and macrophage cells, but which do not typically give rise to erythroid cells or megakaryocytes of the myeloid lineage. Similar to other committed progenitor cells, GMPs lack self-renewal capacity. Murine GMPs may be characterized by the marker phenotype c-Kit$^{hi}$ (CD117) Sca-1$^{neg}$ FcγR$^{hi}$ (CD16) IL-7Rγ$^{neg}$CD34$^{pos}$. Murine GMPs also lack expression of markers B220, CD4, CD8, CD3, Gr-1, Mac-1, and CD90. Human GMPs May be Characterized by the Marker Phenotype CD34$^+$ CD38$^+$ CD123+CD45RA$^+$. Human GMP cell populations are also characterized by the absence of markers CD3, CD4, CD7, CD8, CD10, CD11b, CD14, CD19, CD20, CD56, and CD235a.

"Megakaryocyte/erythroid progenitor cells (MEP)" are derived from the CMPs and are characterized by their capability of differentiating into committed megakaryocyte progenitor and erythroid progenitor cells. MEP give rise to erythroid cells and megakaryocytes, but do not typically give rise to granulocytes, macrophages, or myeloid dendritic cells. Mature megakaryocytes are polyploid cells that are precursors for formation of platelets, a developmental process regulated by thrombopoietin. Erythroid cells are formed from the committed erythroid progenitor cells through a process regulated by erythropoietin, and ultimately differentiate into mature red blood cells. Murine MEPs may be characterized by cell marker phenotype c-Kit$^{hi}$ and IL-7Rα$^{neg}$ and further characterized by marker phenotypes FcγR$^{lo}$ and CD34$^{low}$. Murine MEP cell populations may also be characterized by the absence of markers B220, CD4, CD8, CD3, Gr-1, and CD90. Another exemplary marker phenotype for mouse MEPs is c-kit$^{high}$ Sca-1$^{neg}$ Lin$^{neg/low}$ CD16$^{low}$ CD34$^{low}$. Human MEPs may be characterized by marker phenotypes CD34$^+$ CD38$^+$ CD123$^{neg}$ CD45RA$^{neg}$.

Human MEP cell populations may also be characterized by the absence of markers CD3, CD4, CD7, CD8, CD10, CD11b, CD14, CD19, CD20, CD56, and CD235a.

Further restricted progenitor cells in the myeloid lineage are the granulocyte progenitor, macrophage progenitor, megakaryocyte progenitor, and erythroid progenitor cell types. "Granulocyte progenitor (GP)" cells are characterized by their capability to differentiate into terminally differentiated granulocytes, including eosinophils, basophils, neutrophils. The GP typically do not differentiate into other cells of the myeloid lineage. "Megakaryocyte progenitor cell (MKP)" cells are characterized by their capability to differentiate into terminally differentiated megakaryocytes but generally not other cells of the myeloid lineage (see, e.g., WO 2004/024875).

For the lymphoid lineage, a "committed lymphoid progenitor cell" refers to an oligopotent or unipotent progenitor cell capable of differentiating into any of the terminally differentiated cells of the lymphoid lineage, such as T cell, B cell, NK cell, or lymphoid dendritic cells, but which do not typically differentiate into cells of the myeloid lineage. As with cells of the myeloid lineage, different cell populations of lymphoid progenitors are distinguishable from other cells by their differentiation potential, and the presence of a characteristic set of cell markers. Encompassed within the lymphoid progenitor cells are the "common lymphoid progenitor cells (CLP)", which are oligopotent cells characterized by a capacity to give rise to B-cell progenitors (BCP), T-cell progenitors (TCP), NK cells, and dendritic cells. These progenitor cells have little or no self-renewing capacity, but are capable of giving rise to T lymphocytes, B lymphocytes, NK cells, and lymphoid dendritic cells. The marker phenotypes useful for identifying CLPs are commonly known in the art. For CLP cells of mouse, the cell population may be characterized by the presence of markers as described in, for example, Kondo et. al., (1997) *Cell* 91:661-672, while for human CLPs, a marker phenotype of $CD34^+$ $CD38^+$ $CD10^+$ IL7R+ may be used (Galy et al. (1995) *Immunity* 3:459-473 and Akashi et al. (1999) *Int. J. Hematother.* 69:217-226).

Numerous other suitable cell surface markers are presently known to the skilled artisan and such markers will find advantageous use in the methods and compositions described herein. For instance, several additional potential murine markers have recently been identified for the various myeloid progenitor cell populations based on array analysis of mRNA expression. See, e.g., Iwasaki-Arai et al. (2003) *J. Exp. Med.* 197:1311-1322; Akashi et al. (2000) *Nature* 404:193-197; Miyamoto et al. (2002) *Dev. Cell* 3:137-147; Traver et al. (2001) *Blood* 98:627-635; Akashi et al. (2003) *Blood* 101:383-390; and Terskikh et al. (2003) *Blood* 102: 102:94-101. Based on this same type of mRNA expression analysis, additional cell surface markers such as CD110, CD114, CD116, CD117, CD127, and CD135 may also find use for isolating one or more of the identified myeloid progenitor subpopulations in humans, as described in Manz et al. (2002) *Proc. Natl. Acad. Sci. U.S.A.* 99:11872-11877.

Useful cells of the HSC lineage to be transduced may be capable of differentiating into cells of the myeloid lineage, i.e., granulocytes, macrophages, megakaryocytes, erythroid cells, and/or myeloid dendritic cells. These include, among others, HSCs, and committed myeloid progenitor cells CMPs, GMPs, and MEPs. These cells will have the relevant characteristics, particularly differentiation potential and cell marker characteristics described above. Such cells may be obtained from a variety of sources, including bone marrow, peripheral blood, cord blood, amniotic fluid, and other sources known to harbor HSC lineage cells, including liver, particularly fetal liver. Peripheral and cord blood is a rich source of HSC and related lineage cells.

Cells may be obtained using methods well known in the art. For example, methods for preparing bone marrow cells are described in Sutherland et al. (1991) *Bone Marrow Processing and Purging: A Practical Guide* (Gee, A. P. ed.), CRC Press Inc. Umbilical cord blood or placental cord blood is typically obtained by puncture of the umbilical vein, in both term or preterm, before or after placental detachment (see, e.g., Turner (1992) *Bone Marrow Transplant.* 10:89 and Bertolini et al. (1995) *J. Hematother.* 4:29). HSCs and myeloid progenitor cells may also be obtained from peripheral blood by leukopheresis, a procedure in which blood drawn from a suitable subject is processed by continuous flow centrifugation (e.g., Cobe BCT Spectra blood cell separators) to remove white blood cells while the other blood components are returned to the donor. Another type of isolation procedure is centrifugation through a medium of varying density, such as Ficoll-Hypaque (Amersham Pharmacia Biotech, Piscataway, N.J.).

Cells may be derived from any animal species with a hematopoietic system, as generally described herein. Preferably, suitable animals will be mammals, including, by way of example and without limitation, rodents, rabbits, canines, felines, pigs, horses, cows, primates (e.g., human), and the like. The cells may be obtained from a single subject or a plurality of subjects. A plurality refers to at least two (e.g., more than one) donors. When cells obtained are from a plurality of donors, their relationships may be syngeneic, allogeneic, or xenogeneic, as defined herein.

Where applicable, HSC and related lineage cells may be mobilized from the bone marrow into the peripheral blood by prior administration of cytokines or drugs to the subject (see, e.g., Lapidot et al. (2002) *Exp. Hematol.* 30:973-981). The term "cytokine" refers to compounds or compositions that in the natural state are made by cells and affect physiological states of the cells that produce the cytokine (i.e., autocrine factors) or other cells. Cytokine also encompasses any compounds or compositions made by recombinant or synthetic processes, where the products of those processes have identical or similar structure and biological activity as the naturally occurring forms. Lymphokines refer to natural, synthetic, or recombinant forms of cytokines naturally produced by lymphocytes, including, but not limited to, IL-1, IL-3, IL-4, IL-6, IL-11, and the like. Cytokines and chemokines capable of inducing mobilization include, by way of example and not limitation, granulocyte colony stimulating factor (G-CSF), granulocyte macrophage colony stimulating factor (GM-CSF), erythropoietin (Kiessinger et al. (1995) *Exp. Hematol.* 23:609-612), stem cell factor (SCF), AMD3100 (AnorMed, Vancouver, Canada), interleukin-8 (IL-8), and variants of these factors (e.g., pegfilgastrim and darbopoietin). Combinations of cytokines and/or chemokines, such as G-CSF and SCF or GM-CSF and G-CSF, may act synergistically to promote mobilization and may be used to increase the number of HSC and progenitor cells in the peripheral blood, particularly for subjects who do not show efficient mobilization with a single cytokine or chemokine (see, for example, Morris et al. (2003) *J. Haematol.* 120: 413-423).

Cytoablative agents may be used at inducing doses (i.e., cytoreductive doses) to also mobilize HSCs and progenitor cells, and are useful either alone or in combination with cytokines. This mode of mobilization is applicable when the subject is to undergo myeloablative treatment, and is carried out prior to the higher dose chemotherapy. Cytoreductive drugs for mobilization, include, among others, cyclophosphamide, ifosfamide, etoposide, cytosine arabinoside, and carboplatin (Montillo et al. (2004) *Leukemia* 18:57-62; Dasgupta et al. (1996) *J. Infusional Chemother.* 6:12; and Wright et al. (2001) *Blood* 97:2278-2285).

The HSC lineage cells of interest may also be subjected to further selection, purification, and/or isolation, which may include both positive and negative selection methods, to obtain a substantially pure population of cells. In one aspect, fluorescence activated cell sorting (FACS), also referred to as flow cytometry, is used to sort and analyze the different cell populations. Cells having the cellular markers specific for HSC or a desired HSC lineage cell population are tagged with an antibody, or typically a mixture of antibodies, that bind the cellular markers. Each antibody directed to a different marker is conjugated to a detectable molecule, particularly a fluorescent dye that may be distinguished from other fluorescent dyes coupled to other antibodies. A stream of tagged or "stained" cells is passed through a light source that excites the fluorochrome and the emission spectrum from the cells detected to determine the presence of a particular labeled antibody. By concurrent detection of different fluorochromes, also referred to in the art as multicolor fluorescence cell sorting, cells displaying different sets of cell markers may be identified and isolated from other cells in the population. Other FACS parameters, including, by way of example and not limitation, side scatter (SSC), forward scatter (FSC), and vital dye staining (e.g., with propidium iodide) allow selection of cells based on size and viability. FACS sorting and analysis of HSC and related lineage cells is well known in the art and described in, for example, U.S. Pat. Nos. 5,137,809; 5,750,397; 5,840,580; 6,465,249; Manz et al. (202) *Proc. Natl. Acad. Sci. U.S.A.* 99:11872-11877; and Akashi et al. (200) *Nature* 404:193-197. General guidance on fluorescence activated cell sorting is described in, for example, Shapiro (2003) *Practical Flow Cytomery,* 4th Ed., Wiley-Liss (2003) and Ormerod (2000) *Flow Cytometry: A Practical Approach,* 3rd Ed., Oxford University Press.

Another method of isolating useful cell populations involves a solid or insoluble substrate to which is bound antibodies or ligands that interact with specific cell surface markers. In immunoadsorption techniques, cells are contacted with the substrate (e.g., column of beads, flasks, magnetic particles, etc.) containing the antibodies and any unbound cells removed. Immunoadsorption techniques may be scaled up to deal directly with the large numbers of cells in a clinical harvest. Suitable substrates include, by way of example and not limitation, plastic, cellulose, dextran, polyacrylamide, agarose, and others known in the art (e.g., Pharmacia Sepharose 6 MB macrobeads). When a solid substrate comprising magnetic or paramagnetic beads is used, cells bound to the beads may be readily isolated by a magnetic separator (see, e.g., Kato and Radbruch (1993) *Cytometry* 14:384-92). Affinity chromatographic cell separations typically involve passing a suspension of cells over a support bearing a selective ligand immobilized to its surface. The ligand interacts with its specific target molecule on the cell and is captured on the matrix. The bound cell is released by the addition of an elution agent to the running buffer of the column and the free cell is washed through the column and harvested as a homogeneous population. As apparent to the skilled artisan, adsorption techniques are not limited to those employing specific antibodies, and may use nonspecific adsorption. For example, adsorption to silica is a simple procedure for removing phagocytes from cell preparations.

FACS and most batch wise immunoadsorption techniques may be adapted to both positive and negative selection procedures (see, e.g., U.S. Pat. No. 5,877,299). In positive selection, the desired cells are labeled with antibodies and removed away from the remaining unlabeled/unwanted cells. In negative selection, the unwanted cells are labeled and removed. Another type of negative selection that may be employed is use of antibody/complement treatment or immunotoxins to remove unwanted cells.

It is to be understood that the purification or isolation of cells also includes combinations of the methods described above. A typical combination may comprise an initial procedure that is effective in removing the bulk of unwanted cells and cellular material, for example leukapharesis. A second step may include isolation of cells expressing a marker common to one or more of the progenitor cell populations by immunoadsorption on antibodies bound to a substrate. For example, magnetic beads containing anti-CD34 antibodies are able to bind and capture HSC, CMP, and GMP cells that commonly express the CD34 antigen. An additional step providing higher resolution of different cell types, such as FACS sorting with antibodies to a set of specific cellular markers, may be used to obtain substantially pure populations of the desired cells. Another combination may involve an initial separation using magnetic beads bound with anti-CD34 antibodies followed by an additional round of purification with FACS.

Determining the differentiation potential of cells, and thus the type of stem cells or progenitor cells isolated, is typically conducted by exposing the cells to conditions that permit development into various terminally differentiated cells. These conditions generally comprise a mixture of cytokines and growth factors in a culture medium permissive for development of the myeloid or lymphoid lineage. Colony forming culture assays rely on culturing the cells in vitro via limiting dilution and assessing the types of cells that arise from their continued development. A common assay of this type is based on methylcellulose medium supplemented with cytokines (e.g., MethoCult, Stem Cell Technologies, Vancouver, Canada and Kennedy et al. (1997) *Nature* 386: 488-493). Cytokine and growth factor formulations permissive for differentiation in the hematopoietic pathway are described in Manz et al. (2002) *Proc. Natl. Acad. Sci. U.S.A.* 99:11872-11877; U.S. Pat. No. 6,465,249; and Akashi et al., *Nature* 404:193-197). Cytokines include SCF, FLT-3 ligand, GM-CSF, IL-3, TPO, and EPO. Another in vitro assay is long-term culture initiating cell (LTC-IC) assay, which typically uses stromal cells to support hematopoiesis (see, e.g., Ploemache et al. (1989) *Blood* 74:2755-2763 and Sutherland et al. (1995) *Proc. Natl. Aca. Sci. U.S.A.* 87:3745).

Another type of assay suitable for determining the differentiation potential of isolated cells relies upon in viva administration of cells into a host animal and assessment of the repopulation of the hematopoietic system. The recipient is immunocompromised or immunodeficient to limit rejection and permits acceptance of allogeneic or xenogeneic cell transplants. A useful animal system of this kind is the NOD/SCID (Pflumio et al. (1996) *Blood* 88:3731; Szilvassym et al. (2002) "Hematopoictic Stem Cell Protocol" in *Methods in Molecular Medicine,* Humana Press; Greiner et al. (1998) *Stem Cells* 16:166-177; Piacibello et al. (1999) *Blood* 93:3736-3749) or Rag2 deficient mouse (Shinkai et al. (1992) *Cell* 68:855-867). Cells originating from the infused cells are assessed by recovering cells from the bone marrow, spleen, or blood of the host animal and determining presence of cells displaying specific cellular markers (i.e., marker phenotyping), typically by FACS analysis. Detection of markers specific to the transplanted cells permits distinguishing between endogenous and transplanted cells. For example, antibodies specific to human forms of the cell markers (e.g., HLA antigens) identify human cells when they are transplanted into suitable immunodeficient mouse.

The initial populations of cells obtained by the methods above may be used directly for transduction or frozen for use at a later date. A variety of mediums and protocols for cryopreservation are known in the art. Generally, the freezing medium will comprise DMSO from about 5-10%, 10-90% serum albumin, and 50-90% culture medium. Other additives useful for preserving cells include, by way of example and not limitation, disaccharides such as trehalose (Scheinkonig et al. (2004) *Bone Marrow Transplant.* 34:531-536), or a plasma volume expander, such as hetastarch (i.e., hydroxyethyl starch). In some embodiments, isotonic buffer solutions, such as phosphate-buffered saline, may be used. An exemplary cryopreservative composition has cell-culture medium with 4% HSA, 7.5% dimethyl sulfoxide (DMSO), and 2% hetastarch. Other compositions and methods for cryopreservation are well known and described in the art (see, e.g., Broxmeyer et al. (2003) *Proc. Natl. Acad. Sci. U.S.A.* 100:645-650). Cells are preserved at a final temperature of less than about −135° C.

B. Viral Vectors and Transduction of Hematopoietic Stem Cell Lineages

Viral vectors are well known in the art for transducing target cells and incorporating transgenes.

a) Transgenes

By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene may be a nucleotide sequence, preferably a DNA sequence, that is used to mark the chromosome where it has integrated or may indicate a position where nucleic acid editing, such as by the CRSPR-CAS system, may occur. In this situation, the transgene does not have to comprise a gene that encodes a protein that may be expressed.

A "gene of interest" is a nucleic acid sequence that encodes a protein or other molecule, such as an RNA or targeting nucleic acid sequence, that is desirable for integration in a host cell. The gene of interest may be a 1, 2, 3, 4, 5, 6, 7, 8, 9, 10, or more genes of interest expressed from the same or different vectors.

Genes of interest are useful for modulating the expression and/or activity of target biomolecules either within the transduced cell or expressed for secretion outside of the transduced cell. Generally, genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99 or more as compared to the expression or activity of the target biomolecule which has not been targeted by a modulating agent.

In one embodiment, the gene of interest is useful for overexpressing and/or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulatory sequences like inducible promoters, as described further below.

In one embodiment, the viral vector may be engineered to express the CRISPR-Cas system for precise editing of genomic nucleic acids (e.g., for creating null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47).

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An "RNA coding region" is a nucleic acid that may serve as a template for the synthesis of an RNA molecule, such as an siRNA. "RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example, Coburn and Cullen (2002)

J. Virol. 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more, or any number or range in between, of RNA inhibitory agents, either co-expressed from the same vector or more than one vector, are transduced into cells of interest. Suitable inhibitory RNAs include, but are not limited to siRNAs, shRNAs, miRNAs, Piwis, dicer-substrate 27-mer duplexes, single-stranded interfering RNA, and the like. In particular, the combination of RNA inhibitory technology and lentiviruses as a tool for a gene specific knock-down in animal models is well known in the art (see, for example, U.S. Pat. Publ. 2005/0251872; EP Pat. Publ. 2166107; PCT Pubis. WO 2004/022722 and 2007/109131; Tiscomia et al. (2003) *Proc. Natl. Acad. Sci. U.S.A.* 100:1844-1848; Rubinson et al. (2003) *Nat. Genet.* 33:401-406; and Dann et al. (2006) *Proc. Natl. Acad. Sci. U.S.A.* 103:11246-11251).

siRNAs typically refer to a double-stranded interfering RNA unless otherwise noted. In various embodiments, suitable siRNA molecules include double-stranded ribonucleic acid molecules comprising two nucleotide strands, each strand having about 19 to about 28 nucleotides (i.e. about 19, 20, 21, 22, 23, 24, 25, 26, 27, or 28 nucleotides). Thus, the phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as "interfering RNAs" or "interfering RNA molecules."

Suitable interfering RNAs may readily be produced based on the well-known nucleotide sequences of target biomolecules. In various embodiments interfering RNAs that inhibit target biomolecules may comprise partially purified RNA, substantially pure RNA, synthetic RNA, recombinantly produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, 81%, 82%, 83%, 84%, 85%, 86%, 87%, 88%, 89%, 90%, 91%, 92%, 93%, 94%, 95%, 96%, 97%, 98% 99%, 99, 99.5%, or more, or 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In various embodiments one or both strands of the interfering RNAs may comprise a 3' overhang. As used herein, a "3'overhang" refers to at least one unpaired nucleotide extending from the 3'-end of an RNA strand. Thus in one embodiment, the interfering RNAs comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length. In an illustrative embodiment in which both strands of the interfering RNAs molecule comprise a 3' overhang, wherein the length of the overhangs may be the same or different for each strand. In certain embodiments the 3' overhang is present on both strands of the interfering RNAs and is one, two, or three nucleotides in length. For example, each strand of the interfering RNAs may comprise 3' overhangs of dithymidylic acid ("TT") or diuridylic acid ("uu").

In order to enhance the stability of the interfering RNAs, the 3' overhangs may be also stabilized against degradation. In one embodiment, the overhangs are stabilized by including purine nucleotides, such as adenosine or guanosine nucleotides. In certain embodiments, substitution of pyrimidine nucleotides by modified analogues, e.g., substitution of uridine nucleotides in the 3' overhangs with 2'-deoxythymidine, is tolerated and does not affect the efficiency of RNA interference degradation. In particular, it is believed the absence of a 2' hydroxyl in the 2'-deoxythymidine may significantly enhance the nuclease resistance of the 3' overhang.

Interfering RNAs may be expressed from a vector described herein either as two separate, complementary RNA molecules, or as a single RNA molecule with two complementary regions. Selection of vectors suitable for expressing interfering RNAs, methods for inserting nucleic acid sequences for expressing the interfering RNAs into the vector, and methods of delivering the recombinant plasmid to the cells of interest are well known in the art (Tuschl (2002) *Nat. Biotechnol.* 20: 446-448; Brummelkamp et al. (2002) *Science* 296:550 553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508).

In certain embodiments, the interfering RNAs may be delivered as a small hairpin RNA or short hairpin RNA (shRNA) (see, for example, U.S. Pat. Nos. 8,697,359 and 8,642,569), shRNA is a sequence of RNA that makes a tight hairpin turn that may be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that as bound to it.

In certain embodiments, the sense sequence of the shRNA will be from about 19 to about 30, more nucleotides (e.g. about 19, 20, 21, 22, 23, 24, 25, 26, 27, 28, 29, or 30 nucleotides) in length, more typically from about 19 to about 22 nucleotides in length, the antisense sequence will be from about 19 to about 30, more typically from 19 to about 22 nucleotides (e.g. about 19, 20, 21 or 22 nucleotides), in length, and the loop region will be from about 3 to about 19 nucleotides (e.g., about 3, 4, 5, 6, 7, 8, 9, 10, 11, 12, 13, 14, 15, 16, 17, 18, and 19 nucleotides) in length. In some embodiments, the sense and antisense sequences are the same length, i.e. the shRNA will form a symmetrical hairpin, but this is not necessarily the case. In some cases, the sense or antisense strand may be shorter than its complementary strand, and an asymmetric hairpin is formed. Further, while in some instances the base pairing between the sense and antisense sequences is exact, this also need not be the case. Thus, some mismatch between the sequences may be tolerated, or even desired, e.g. to decrease the strength of the hydrogen bonding between the two strands. However, in one illustrative embodiment, the sense and antisense sequences are the same length, and the base pairing between the two is exact and does not contain any mismatches. The shRNA molecule may also comprise a 5'-terminal phosphate group that may be chemically modified. In addition, the loop portion of the shRNA molecule may comprise, for example, nucleotides, non-nucleotides, linker molecules, conjugate molecules, etc.

In certain embodiments, the PIWI RNA pathway is used to provide inhibition of target biomolecules. Piwi-interacting RNAs (piRNAs) were identified through association with Piwi proteins in mammalian testes (Aravin et al. (2006); Girard et al. (2006); Grivna et al. (2006), Lau et al. (2006). piRNAs and methods of making and using same to target and degrade nucleic acids are well known in the art (see, for example, U.S. Pat. Publ. 2011-0207625). These RNAs range from 26-30 nucleotides in length and are produced from discrete loci. Generally, genomic regions spanning 50-100 kB in length give rise to abundant piRNAs with profound strand asymmetry. Although the piRNAs themselves are not conserved, even between closely related species, the positions of piRNA loci in related genomes are conserved, with virtually all major piRNA-producing loci having syntenic counterparts in mice, rats and humans (Girard et al. (2006)). The loci and consequently the piRNAs themselves are relatively depleted of repeat and transposon sequences, with only 17% of human piRNAs corresponding to known repetitive elements as compared to a nearly 50% repeat content for the genome as a whole. In certain embodiments, methods are provided for inhibiting such targets in a cell, comprising administering an effective amount of a siRNA/shRNA/piwiRNA to the cell, such that target mRNA is degraded.

As described below, internal promoters may be engineered into viral vectors in order to allow for the independent expression of more than one gene of interest. If a second or additional gene of interest is included, an internal ribosomal entry site (IRES) sequence may be included (see, for example, U.S. Pat. No. 4,937,190). The IRES sequence may facilitate the expression of the reporter gene and may be used to create multigene, or polycistronic, messages. IRES elements are able to bypass the ribosome scanning model of 5'-methylated cap-dependent translation and begin translation at internal sites (Pelletier and Sonenberg, 1988). IRES elements are well known in the art and be isolated from, for example, at least two members of the picornavirus family (polio and encephalomyocarditis) have been described (Pelletier and Sonenberg, 1988), as well as from a mammalian message (Macejak and Sarnow, 1991). IRES elements may be linked to heterologous open reading frames. Multiple open reading frames may be transcribed together, each separated by an IRES, creating polycistronic messages. By virtue of the IRES element, each open reading frame is accessible to ribosomes for efficient translation. Multiple genes may be efficiently expressed using a single promoter/enhancer to transcribe a single message.

In certain embodiments of the invention, cells transduced with the lentivectors of the present invention may be identified in vitro or in vivo by including a marker in the expression vector. Such markers would confer an identifiable change to the transduced cell permitting easy identification of cells containing the expression vector. For example, a gene of interest encoding a marker protein may be placed after the primary gene of interest that is, for example, an RNA interfering nucleic acid, to allow for identification of cells that are expressing the desired protein.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genetic constructs that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Many useful reporter markers are known and include, for example, a fluorescence marker, preferably selected from green fluorescent protein (GFP), enhanced GFP (eGFP), DsRed, AsRed, HeRed, Tomatoe, Cherry, Katushka, and variants thereof (see, for example, U.S. Pat. Nos. 5,487,932 and 5,464,763). Examples of other useful reporters include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

b) Viral Vectors

In general, viral vectors are plasmid-based or virus-based, and are configured to carry the essential sequences for incorporating foreign nucleic acid, for selection and for transfer of the nucleic acid into a host cell. The viral construct is a nucleotide sequence that comprises sequences necessary for the production of recombinant retrovirus in a packaging cell. In one embodiment, the viral construct additionally comprises genetic elements that allow for the desired expression of a gene of interest in the host cell. Generation of the viral construct may be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. (1989) Molecular Cloning: A Laboratory Manual. Cold Spring Harbor Laboratory Press, N.Y.; Coffin et al. (997) Retroviruses. Cold Spring Harbor Laboratory Press, N.Y.; and "RNA Viruses: A Practical Approach" (Alan J. Cann, Ed., Oxford University Press, 2000).

Exemplary viral vectors include, for example, adenovirus vectors, adeno-associated virus vectors, retrovirus vectors, and lentivirus vectors. In some embodiments, viral vectors that integrate transgenes are used (e.g., virus other than adenoviral vectors). Exemplary types of viruses include HSV (herpes simplex virus), AAV (adeno associated virus), HIV (human immunodeficiency virus), BIV (bovine immunodeficiency virus), and MLV (murine leukemia virus). Nucleic acids may be transduced in any desired format that provides sufficiently efficient delivery levels, including in virus particles. A viral gene delivery vehicle may optionally comprise viral sequences such as a viral origin of replication or packaging signal. These viral sequences may be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al. (1983) Cell 33:153; Cane and Mulligan (1984) Proc. Natl. Acad. Sci. U.S.A. 81:6349; Miller et al. (1990) Hum. Gene Therap. 1:5-14; U.S. Pat. Nos. 4,405,712, 4,861,719, and 4,980,289; and PCT Publs. WO 89/02,468, WO 89/05,349, and WO 90/02,806. Numerous retroviral gene delivery vehicles may be utilized in the present invention, including for example those described in EP Pat. Publ. 0415731; PCT Publs. WO 90/07936, WO 94/03622, WO 93/25698, and WO 93/25234; U.S. Pat. No. 5,219,740; PCT. Publs. WO 93/11230 and WO 93/10218; Vile and Hart (1993) Cancer Res. 53:3860-3864; Vile and Hart (1993) Cancer Res. 53:962-967; Ram et al. (1993) Cancer Res. 53:83-88; Takamiya et al. (1992) J. Neurosci. Res. 33:493-503; Baba et al. (1993) J. Neurosurg. 79:729-735; U.S. Pat. No. 4,777,127; G.B. Patent No. 2,200, 651; EP. Pat. Publ. 0345242; and PCT Publs. WO91/02805.

Other viral vector systems that may be used to deliver a polynucleotide of the invention have been derived from herpes virus, e.g., Herpes Simplex Virus (U.S. Pat. No. 5,631,236 and PCT Publ. WO 00/08191), vaccinia virus (Ridgeway (1988) "Mammalian expression vectors," In: Rodriguez and Denhardt, eds. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Exemplary viruses include an alphavirus, a poxivirus, an arena virus, a vaccinia virus, a polio virus, and the like. They offer several attractive features for various mammalian cells (see, for example, Friedmann (1989) Science 244:1275-1281; Ridgeway (1988) supra; Baichwal and Sugden (1986) supra; and Horwich et al. (1990) J. Virol. 64:642-650).

In some embodiments, lentiviral vectors are useful. Numerous lentiviruses suitable for use in the present invention are well known in the art. "Lentivirus" refers to a genus of retroviruses that are capable of infecting dividing and non-dividing cells. Lentiviruses may infect nondividing cells owing to the karyophilic properties of their preintegration complex, which allow for its active import through the nucleopore. Several examples of lentiviruses include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. The 5' and 3' LTR's serve to promote transcription and polyadenylation of the virion RNAs. The LTR contains all other cis-acting sequences necessary for viral replication. Lentiviruses have additional genes including vif, vpr, tat, rev, vpu, nef and vpx. Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins. Engineered lentiviral vectors are also known that may transduce hematopoietic stem cells and HSC lineages (see, for example, "RNA Viruses: A Practical Approach" (Alan J. Cann, Ed., Oxford University Press, (2000); O Narayan and Clements (1989) J. Gen. Virol. 70:1617-1639; Fields et al. (1990) Fundamental Virology, Raven Press.; Miyoshi et al. (1998)J. Virol. 72:8150-8157; U.S. Pat. Nos. 5,994,136, 6,013,516, 8,551,773, and 8,361,787; Evans et al. (1999) Hum. Gene Ther. 10:1479-1489; Case et al. (1999) Proc. Natl. Acad. Sci. U.S.A. 96:2988-2993; Uchida et al. (1998) Proc. Natl. Acad. Sci. U.S.A. 95:11939-11944; Miyoshi et al. (1999) Science 283:682-686; Sutton et al. (1998) J. Virol. 72:5781-5788).

The viral virus vectors may be psedudotyped. A "pseudotyped" virus is a viral particle having an envelope protein that is from a virus other than the virus from which the RNA genome is derived. The envelope protein may be from a different virus. For example, an envelope protein is the vesicular stomatitius virus G (VSV G) protein or from measles virus. However, to eliminate the possibility of human infection, viruses may alternatively be pseudotyped with ecotropic envelope protein that limit infection to a specific species, such as mice or birds. For example, in one embodiment, a mutant ecotropic envelope protein is used, such as the ecotropic envelope protein 4.17 (see, for example, Powell et al. (2000) *Nat. Biotech.* 18:1279-1282).

The viral virus vectors may also be self-inactivating. For example, a "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. For example, a deletion in the U3 region of the 3' LTR of the vector DNA, i.e., the DNA used to produce the vector RNA may be made. Thus, during reverse transcription, this deletion is transferred to the 5' LTR of the proviral DNA. It is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function spread out over U3, R and U5. Accordingly, it is desirable to eliminate as many of the transcriptionally important motifs from the LTR as possible while sparing the polyadenylation determinants. The LTR may be rendered about 80%, 81%, 82%, 83%, 84%, 85%, 86%, 87%, 88%, 89%, 90%, 91%, 92%, 93%, 94%, 95% 96% 97%, 98%, to about 99% transcriptionally inactive.

Self-inactivating 3' LTRs and other viral self-inactivating methods and reagents are well known in the art (see, for example, Zuffrey et al. (1998) *J. Virol.* 72:9873-9880; Miyoshi et al. (1998) *J. Virol.* 72:8150-8157; and Iwakuma et al. (1999) *Virol.* 261:120-132).

Other elements commonly found in viral vectors and generally operably linked to genes of interest in order to enhance the expression or utility of the viral vectors are well known and described further below.

c) Enhancers, Promoters, and Inducible Forms Thereof

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter, or other regulatory element or useful element of the vector, is in a correct functional location and/or orientation in relation to a nucleic acid sequence to regulate the sequence (e.g., control transcriptional initiation and/or expression of that sequence).

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, the 5' end of the transcription initiation site of the transcriptional reading frame is placed "downstream" of (i.e., 3' of) the chosen promoter. The spacing between promoter elements frequently is flexible, so that promoter function is preserved when elements are inverted or moved relative to one another. In the tk promoter, the spacing between promoter elements may be increased to 50 bp apart before activity begins to decline. Depending on the promoter, it appears that individual elements may function either cooperatively or independently to activate transcription.

In addition, a specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons may be either natural or synthetic. The efficiency of expression may be enhanced by the inclusion of appropriate transcription enhancer elements.

A promoter may or may not be used in conjunction with an "enhancer," which refers to a cis-acting regulatory sequence involved in the transcriptional activation of a nucleic acid sequence. Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way. For example the CMV enhancer (Karasuyama et al. (1989) *J. Exp. Med.* 169:13) may be used in combination with the chicken β-actin promoter (see, e.g., JP 1990005890-A1). Again, one of skill in the art will be able to select the appropriate enhancer based on the desired expression pattern.

A promoter may be one naturally associated with a nucleic acid sequence, as may be obtained by isolating the 5' non-coding sequences located upstream of the coding segment and/or exon. Such a promoter may be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906). Furthermore, it is contemplated the control sequences that direct transcription and/or expression of sequences within non-nuclear organelles such as mitochondria, chloroplasts, and the like, may be employed as well. Control sequences comprising promoters, enhancers and other locus or transcription controlling/modulating elements are also referred to as "transcriptional cassettes".

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. (1989) supra). The promoters employed may be constitutive, tissue-specific, cell-specific, developmental stage-specific, inducible, and/or useful under the appropriate conditions to direct high level expression of the introduced DNA segment, such as is advantageous for gene therapy or for applications such as the large-scale production of recombinant proteins and/or peptides. The promoter may be heterologous or endogenous. Use of a T3, T7 or SP6 cytoplasmic expression system is another possible embodiment. Eukaryotic cells may support cytoplasmic transcription from certain bacterial promoters if the appropriate bacterial polymerase is provided, either as part of the delivery complex or as an additional genetic expression construct. To determine whether a particular promoter is useful, a selected promoter may be tested in the construct in vim in an HSC lineage cell and, if the promoter is capable of promoting expression of the transgene at a detectable signal-to-noise ratio, it will generally be useful in accordance with the present invention. A desirable signal-to-noise ratio is one between about 10 and about 200, a more desirable signal-to-noise ratio is one 40 and about 200, and an even more desirable signal-to-noise ratio is one between about 150 and about 200. One means of testing such a promoter, described in more detail herein below, is through the use of a signal generating transgene such as a reporter, like a fluorescent protein such as the green fluorescent protein (GFP).

Non-limiting examples of promoters that may be used include the promoter for ubiquitin. CMV (U.S. Pat. No. 5,168,062 and Karasuyama et al. (1989) *J. Exp. Med.* 169:13), β-actin (Gunning et al. (1987) *Proc. Natl. Acad. Sci. U.S.A.* 84:4831-4835), and pgk (U.S. Pat. Nos. 4,615, 974 and 5,104,795; Adra et al. (1987) *Gene* 60:65-74; Singer-Sam et al. (1984) *Gene* 32:409-417; and Dobson et al. (1982) *Nucl. Acids Res.* 10:2635-2637). Alternatively, the promoter may be a tissue specific promoter. Several non-limiting examples of tissue specific promoters that may be used include Ick (see, for example, Garvin et al. (1988) *Mol. Cell. Biol.* 8:3058-3064 and Takadera et al. (1989) *Mol. Cell. Biol.* 9:2173-2180), myogenin (Yee et al. (1993) *Genes Dev.* 7:1277-1289), and thy 1 (Gundersen et al. (1992) *Gene* 113:207-214). In addition, promoters may be selected to allow for inducible expression of the transgene.

For expressing short RNAs, such as interfering RNAs, RNA Polymerase III promoters are well known to one of skill in the art. For example, a wide range of RNA Polymerase III promoters are disclosed in Paule and White (2000) *Nucl. Acids Res.* 28:1283-1298. The definition of RNA Polymerase III promoters also include any synthetic or engineered DNA fragment that may direct RNA Polymerase III to transcribe a downstream RNA coding sequence. Suitable promoters include, but are not limited to, the U6 or HI RNA pol III promoter sequences and the cytomegalovirus promoter.

Further, viral vector promoters, such as the RNA Polymerase III (Pol III) promoter or other promoters used as part of the viral vector, may be inducible. Any suitable inducible promoter may be used with the methods of the present invention and such promoters are well known in the art (see, for example, PCT Publ. WO 2004/056964; U.S. Pat. No. 8,679,845; and U.S. Pat. Publ. 2010/0077495). Transcription-regulatory elements conferring inducibility on the promoters may be placed within the promoter region, such as between the proximal sequence element (PSE) and the transcription start site, upstream or downstream from the TATA box. Such sequences may also be placed outside the promoter, such as downstream from the end of an interfering RNA sequence. In addition, a viral vector contain 1, 2, 3, 4, 5, 6, 7, 8, 9, 10, or more of such inducibility conferring elements in order to more or less tightly regulate transcription in response to the inducing signal.

Useful inducible Pol III promoters include tetracycline responsive promoters (see, for example, Ohkawa and Taira (2000) *Hum. Gene Therap.* 11:577-585 and Meissner et al. (2001) *Nucl. Acids Res.* 29:1672-1682), operator sequences (tetO) of the *E. coli* tetracycline resistance operon (Czauderna et al. (2003) *Nucl. Acids Res.* 31:e127; Matsukura er al. (2003) *Nucl. Acids Res.* 31:e77; van de Wetering et al. (2003) *EMBO Rep.* 4:609-615; and Ohkawa et al. (2000) *Hum. Gene Ther.* 11:577-585). Many inducible promoters may be used as a cis-regulatory element and these commonly, but not necessarily, use an element that serves a landing pad function of providing a place to which a tethering factor (a sequence-specific DNA binding protein) may bind to the DNA and bring a diversification factor, fused to the tethering factor, into sufficient proximity of the coding region so that diversification of the coding region is capable of reversible regulation. A tethering factor is one that binds to the cis-regulatory element in a sequence-specific manner. In the embodiments in which LacO serves as a cis-regulatory element, the Lac repressor, LacI, may serve as the tethering factor, and its binding to the cis-regulatory element, LacO, may be regulated by isopropyl-β-D-thio-galactoside (IPTG). In the absence of IPTG, Lad binds LacO and diversification is accelerated (or otherwise regulated) by the presence of the diversification factor. IPTG may be added in the event that a halt or reduction in activity of the diversification factor is desired. In embodiments in which TetO serves as the cis-regulatory element, TetR may be a suitable tethering factor, and the activity of the diversification factor may be regulated by tetracycline or doxycycline. Other transcription-regulatory elements that allow or inducible expression are well known in the art and may be inserted into the promoter region for controlled expression of genes of interest. For example, LPTG-inducible systems based on LacO and LacI repressors are well known in the art, as are inducible systems based on Cre, GalO, MTII (phorbol ester, TFA), MMTV (glucocorticoids), beta-interferon (poly(rl) or poly(rc)), adenovirus 5 E2 (E1A), collagenase (phorbol ester, TFA), and the like. For RNA Polymerase I- or Pol LI-based transcription units, well-established inducible systems such as tetracycline transactivator systems, reverse tetracycline transactivator systems, and ecdysone systems may be used.

Additional regulatory elements are also well known that may enhance expression of the gene of interest. One type of posttranscriptional regulatory sequence is an intron positioned within the expression cassette, which may serve to stimulate gene expression. Since introns placed in such a manner may expose the RNA transcript of the gene of interest to the normal cellular splicing and processing mechanisms, it may be desirable to locate intron-containing transgenes in an orientation opposite to that of the vector genomic transcript. Alternatively, a method of enhancing expression of a gene of interest is through the use of a posttranscriptional regulatory element which does not rely on splicing events, such as the posttranscriptional processing element of herpes simplex virus, the posttranscriptional regulatory element of the hepatitis B virus (HPRE) or that of the woodchuck hepatitis virus (WPRE), which contains an additional cis-acting element not found in the HPRE. The regulatory element is positioned within the vector so as to be included in the RNA transcript of the transgene, but outside of stop codon of the transgene translational unit. The use of such regulatory elements are particularly preferred in the context of modest promoters, but may be contraindicated in the case of very highly efficient promoters.

d) Other Vector Elements

Vectors of the present invention may include a multiple cloning site (MCS), which is a nucleic acid region that contains multiple restriction enzyme sites, any of which may be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

The vectors useful for the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements may serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. For example, Pol III terminators preferably comprise of stretches of 4 or more thymidine ("T") residues. In a preferred embodiment, a cluster of 5 consecutive Ts is linked immediately downstream of the RNA coding region to serve as the terminator. In such a construct pol III transcription is terminated at the second or third T of the DNA template, and thus only 2 to 3 uridine ("U") residues are added to the 3' end of the coding sequence. In certain embodiments, the termination signal may be a lack of transcribable or translatable sequence, such as due to a sequence truncation.

In eukaryotic gene expression, a polyadenylation signal is generally added in order to effect proper polyadenylation of the transcript. The nature of the polyadenylation signal is not believed to be crucial to the successful practice of the invention, and any such sequence may be employed. Some examples include the SV40 polyadenylation signal or the bovine growth hormone polyadenylation signal, convenient and known to function well in various target cells. Polyadenylation may increase the stability of the transcript or may facilitate cytoplasmic transport.

In order to propagate a vector of the invention in a host cell, it may contain one or more origins of replication sites (often termed "ori"), which is a specific nucleic acid sequence at which replication is initiated. Alternatively an autonomously replicating sequence (ARS) may be employed if the host cell is yeast.

e) Production of Virus

Any method known in the art may be used to produce infectious retroviral particles whose genome comprises an RNA copy of the viral construct described above. Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Useful packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins (see, for example, U.S. Pat. No. 6,218,181). Alternatively a packaging cell line may be transiently transfected with plasmids comprising nucleic acid that encodes the necessary viral proteins. In one embodiment a packaging cell line that stably expresses the viral proteins required for packaging the RNA genome is transfected with a plasmid comprising the viral construct described above. In another embodiment a packaging cell line that does not stably express the necessary viral proteins is co-transfected with two or more plasmids (see, for example, Yee e al. (1994) *Meth. Cell. Biol.* 43A:99-112). In some embodiments, the packaging cell line may not express envelope gene products. In this case, the packaging cell line will package the viral genome into particles that lack an envelope protein. As the envelope protein is responsible, in part, for the host range of the viral particles, the viruses may be pseudotyped as described above. In other embodiments, RNA interference activity of the packaging cells may be suppressed in order to improve the production of recombinant virus. This includes, without limitation, the use of cotransfection or stable transfection of constructs expressing siRNA molecules to inhibit Dicer, an RNase III family member of ribonuclease which is essential for RNA interference (Hammond et al. (20011) *Nat. Rev. Genet.* 2:110-119). The recombinant virus is then preferably purified from the packaging cells, titered and diluted to the desired concentration according to standard protocols well known in the art.

f) Delivery of Virus

Target cells may be transduced in any way that allows the virus to contact the target cells in which delivery of a sequence containing a gene of interest is desired according to well-known methods in the art (see, for example U.S. Pat. No. 8,552,150). In some embodiments, a suitable amount of virus is introduced into a subject directly (in vivo), for example though injection into the host's body. In some preferred embodiments, the viral particles are injected into a subject's peripheral blood stream. In other preferred embodiments, the viral particles are injected into a subject through intra-dermal injection, subcutaneous injection, intra-peritoneal cavity injection, or intra-venal injection. The virus may be delivered using a subdermal injection device, such as those disclosed in U.S. Pat. Nos. 7,241,275, 7,115,108, 7,108,679, 7,083,599, 7,083,592, 7,047,070, 6,971,999, 6,808,506, 6,780,171, 6,776,776, 6,689,118, 6,670,349, 6,569,143, 6,494,865, 5,997,501, 5,848,991, 5,328,483, 5,279,552, 4,886,499. Other injection locations also are suitable, such as directly into organs comprising target cells. For example intra-lymph node injection, intra-spleen injection, or intra-bone marrow injection may be used to deliver virus to the lymph node, the spleen and the bone marrow, respectively. Transduced cell populations of interest may then be selected.

In other embodiments of the present invention, a suitable amount of virus is introduced into target cells obtained from a subject (ex vivo), for example through incubation of the virus with target primary cells or target cells in culture. The target cells may be cells obtained from bone marrow, fetal liver, peripheral blood, amniotic fluid, cord blood, and the like. Methods to obtain cells from a subject are well known in the art as described above. The virus may be suspended in media and added to the wells of a culture plate, tube or other container. The media containing the virus may be added prior to the plating of the cells or after the cells have been plated. Preferably cells are incubated in an appropriate amount of media to provide viability and to allow for suitable concentrations of virus in the media such that infection of the host cell occurs.

In still other embodiments, target cells are provided and contacted with the virus in vitro, such as in culture plates. The cells may be incubated with the virus for a sufficient amount of time to allow the virus to infect the cells. Preferably the cells are incubated with virus for at least 1 hour, more preferably at least 5 hours and even more preferably at least 10 hours.

In ex vivo, in vitro, and in vivo delivery embodiments, any concentration of virus that is sufficient to infect the desired target cells may be used, as may be readily determined by the skilled artisan. When the target cell is to be cultured, the concentration of the viral particles is at least 1 PFU/µl, more preferably at least 10 PFU/µl, even more preferably at least 400 PFU/µl and even more preferably at least $1\times10^4$ PFU/µl. The titer of the virus may be adjusted to allow for, on average, 1, 2, 3, 4, 5, or more independent cellular transductions with independent viral constructs. In one embodiment, the viral titer is adjusted to allow for 1 or fewer such cellular transduction events in order to prevent multiple integration events.

The methods of infecting cells disclosed above do not depend upon individual-specific characteristics of the cells. As a result, they are readily extended to all mammals. In some embodiments the recombinant virus is delivered to a human or to human HSC cell lineages. In other embodiments, the recombinant virus is delivered to a mouse or to mouse HSC cell lineages. In still other embodiments, the recombinant virus is delivered to an animal other than a human or a mouse, or to cells from an animal other than a human or a mouse.

As discussed above, the recombinant virus may be pseudotyped to confer upon it a broad host range as well as target cell specificity. One of skill in the art would also be aware of appropriate internal promoters to achieve the desired expression of a polynucleotide or gene of interest in a particular animal species. Thus, one of skill in the art will be able to modify the method of infecting dendritic cells derived from any species.

The transduced cells may be analyzed, for example for integration, transcription, and/or expression of genes of interest, the number of copies of the gene integrated, and the location of the integration. Such analysis may be carried out at any time and may be carried out by any methods known in the art. Incubator animals in which a recombinant virus or virus-infected target cells are administered may be analyzed for location of infected cells, expression of the virus-delivered gene of interest, modulation of an immune response, and/or monitored for symptoms associated with a disease or disorder by any methods known in the art.

C. Transplantation and Selection of Transduced Cells in Incubator Animals

Transduced HSC lineage cells may be transplanted into incubator animals such that they proliferate, develop, and/or differentiate in an in vivo environment. Transduced cell populations of interest may then be selected from the incubator animals.

"Incubator animals" are host animals in which transduced HSC lineage cells may proliferate, develop, and/or differentiate in an in vivo environment. The host animals, animal ages, transplantation routes, cellular isolation methods, marker phenotyping methods, and the like are not particularly restricted and include all of the various animals from which the transduced HSC lineage cells were obtained, as described above. Following transduction, the transduced HSC lineage cells may be introduced or re-introduced into an incubator animal. In some embodiments, the cells may be introduced into the peripheral blood stream by, for example, intravenous infusion. The cells introduced into a subject may be cells derived from that subject, to avoid an adverse immune response. Cells also may be used that are derived from a donor subject having a similar immune background.

Other cells also may be used, including those designed to avoid an adverse immunogenic response.

In one embodiment, incubator animals are autologous with respect to the transduced HSC lineage cells. "Autologous" refers to deriving from or originating in the same subject or patient. An "autologous transplant" refers to the harvesting and reinfusion or transplant of a subject's own cells or organs. Exclusive or supplemental use of autologous cells may eliminate or reduce many adverse effects of administration of the cells back to the host, particular graft versus host reaction.

In another embodiment, incubator animals are allogeneic with respect to the transduced HSC lineage cells. "Allogeneic" refers to deriving from, originating in, or being members of the same species, where the members are genetically related or genetically unrelated but genetically similar. An "allogeneic transplant" refers to transfer of cells or organs from a donor to a recipient, where the recipient is the same species as the donor.

In still another embodiment, incubator animals are mismatched allogeneic with respect to the transduced HSC lineage cells. "Mismatched allogeneic" refers to deriving from, originating in, or being members of the same species having non-identical major histocompatibility complex (MHC) antigens (i.e., proteins) as typically determined by standard assays used in the art, such as serological or molecular analysis of a defined number of MHC antigens. A "partial mismatch" refers to partial match of the MHC antigens tested between members, typically between a donor and recipient. For instance, a "half mismatch" refers to 50% of the MHC antigens tested as showing different MHC antigen type between two members. A "full" or "complete" mismatch refers to all MHC antigens tested as being different between two members.

Determining the degree of MHC mismatch may be accomplished according to standard tests known and used in the art. For instance, there are at least six major categories of MHC genes in humans, identified as being important in transplant biology. HLA-A, HLA-B, HLA-C encode the HLA class I proteins while HLA-DR, HLA-DQ, and HLA-DP encode the HLA class II proteins. Genes within each of these groups are highly polymorphic, as reflected in the numerous HLA alleles or variants found in the human population, and differences in these groups between individuals is associated with the strength of the immune response against transplanted cells. Standard methods for determining the degree of MHC match examine alleles within HLA-B and HLA-DR, or HLA-A, HLA-B and HLA-DR groups. Thus, tests may be made of at least 4, and even 5 or 6 MHC antigens within the two or three HLA groups, respectively.

In serological MHC tests, antibodies directed against each HLA antigen type are reacted with cells from one subject (e.g., donor) to determine the presence or absence of certain MHC antigens that react with the antibodies. This is compared to the reactivity profile of the other subject (e.g., recipient). Reaction of the antibody with an MHC antigen is typically determined by incubating the antibody with cells, and then adding complement to induce cell lysis (i.e., lymphocytotoxicity testing). The reaction is examined and graded according to the amount of cells lysed in the reaction (see, for example, Mickelson and Petersdorf (1999) *Hematopoietic Cell Transplantation*, Thomas, E. D. et al. eds., pg 28-37, Blackwell Scientific, Maiden, Mass.). Other cell-based assays include flow cytometry using labeled antibodies or enzyme linked immuno assays (ELISA).

Molecular methods for determining MHC type are well known and generally employ synthetic probes and/or primers to detect specific gene sequences that encode the HLA protein. Synthetic oligonucleotides may be used as hybridization probes to detect restriction fragment length polymorphisms associated with particular HLA types (Vaughn (2002) *Method. Mol. Biol. MHC Protocol.* 210:45-60). Alternatively, primers may be used for amplifying the HLA sequences (e.g., by polymerase chain reaction or ligation chain reaction), the products of which may be further examined by direct DNA sequencing, restriction fragment polymorphism analysis (RFLP), or hybridization with a series of sequence specific oligonucleotide primers (SSOP) (Petersdorf et al. (1998) *Blood* 92:3515-3520; Morishima et al. (2002) *Blood* 99:4200-4206; and Middleton and Williams (2002) *Method. Mol. Biol. MHC Protocol.* 210:67-112).

In yet another embodiment, incubator animals are syngeneic with respect to the transduced HSC lineage cells. "Syngeneic" refers to deriving from, originating in, or being members of the same species that are genetically identical, particularly with respect to antigens or immunological reactions. These include identical twins having matching MHC types. Thus, a "syngeneic transplant" refers to transfer of cells or organs from a donor to a recipient who is genetically identical to the donor.

In another embodiment, incubator animals are xenogeneic with respect to the transduced HSC lineage cells. "Xenogeneic" refers to deriving from, originating in, or being members of different species, e.g., human and rodent, human and swine, human and chimpanzee, etc. A "xenogeneic transplant" refers to transfer of cells or organs from a donor to a recipient where the recipient is a species different from that of the donor. In one embodiment, the incubator animal may be "humanized" in order to be compatible with human transduced HSC lineage cells. The term "immune-system humanized" refers to an animal such as a mouse comprising human HSC lineage cells and human acquired and innate immune cells, wherein the human HSC lineage cells and human acquired and innate immune cells differentiated from the HSC lineage cells survive without being rejected from the host animal, thereby allowing human hematopoiesis and both acquired and innate immunity to be reconstituted in the host animal. Acquired immune cells include T cells and B cells. Innate immune cells include macrophages, granulocytes (basophils, eosinophils, neutrophils), DCs, NK cells and mast cells. Representative, non-limiting examples include SCID-hu, Hu-PBL-SCID, Hu-SRC-SCID, NSG (NOD-SCID IL2r-gamma(null)), NOG (NOD-SCID IL2r-gamma(truncated)), BRG (BALB/c-Rag2(null)IL2r-gamma (null))), and H2dRG (Stock-H2d-Rag2(null)IL2r-gamma (null)) mice (see, for example, Shultz et al. (2007) *Nat. Rev. Immunol.* 7:118: Pearson et al. (2008) *Curr. Protocol. Immunol.* 15:21; Brehm et al. (2010) *Clin. Immunol.* 135:84-98), as well as related null mutants of immune-related genes like Rag1, Rag2, IL2rg, or Prf1, allow for efficient engraftment of human immune cells in mice (see, for example, PCT Publ. WO2013/062134).

Besides the species or immunological match between the transduced HSC lineage cells and the incubator animal, the incubator animal may be distinguished from the transduced HSC lineage cells in other ways. For example, the incubator animal may be congenic with respect to the transduced HSC lineage cells. "Congenic" refers to deriving from, originating in, or being members of the same species, where the members are genetically identical except for a small genetic region, typically a single genetic locus (i.e., a single gene). A "congenic transplant" refers to transfer of cells or organs from a donor to a recipient, where the recipient is genetically identical to the donor except for a single genetic locus. For example, CD45 exists in several allelic forms and congenic mouse lines exist in which the mouse lines differ with respect to whether the CD45.1 or CD45.2 allelic versions are expressed.

In one embodiment, the incubator animal is immunocompromised. An "immunocompromised" animal is an animal who is incapable of developing or unlikely to develop a robust immune response due to a lack or reduction in functioning mature immune system cells, such as B cells and/or T cells. Immunocompromised subjects are more susceptible to opportunistic infections, for example viral, fungal, protozoan, or bacterial infections, prion diseases, and certain neoplasms.

In some embodiments, the immunocompromised incubator animal is "immunodeficient" in which no native host immune response may be mounted. In one embodiment, immunodeficient mice are useful. For example, such mice may have severe combined immune deficiency. The term "severe combined immune deficiency (SCID)" refers to a condition characterized by absence of T cells and lack of B cell function. Common forms of SCID include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−). IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+). In one embodiment, the immunodeficient mouse used in the present invention is a mouse having the severe combined immunodeficiency mutation (Prkdc$^{scid}$), commonly referred to as the scid mutation. The scid mutation is well-known and located on mouse chromosome 16 (sec. for example, Bosma et al. (1989) *Immunogenet.* 29:54-56). Mice homozygous for the scid mutation are characterized by an absence of functional T cells and B cells, lymphopenia, hypoglobulinemia and a normal hematopoietic microenvironment. The scid mutation may be detected, for example, by detection of markers for the scid mutation using well-known methods.

Immunocompromised and immunodeficient incubator animals allow for ablation of the native host immune system such that the immune system may be repopulated substantially or completely from the transplanted transduced HSC lineage cells. Aside from genetic manipulations, incubator animals may be rendered immunocompromised or immunodeficient using any number of well-known techniques. For example, they may be conditioned with sub-lethal irradiation or lethal irradiation with high frequency electromagnetic radiation, generally using gamma radiation, or treated with a radiomimetic drug such as busulfan or nitrogen mustard, or treated with immunotherapy to deplete immune system-mediating cell populations (see, for example, Hayakawa et al. (2009) *Stem Cells* 27:175-182).

Transplantation of cells into incubator animals may be accomplished using methods generally known in the art. For example, incubator animals of interest may be engrafted with transplanted transduced HSC lineage cells by various routes. Such routes include, but are not limited to, intravenous administration, injection into the femur bone marrow cavity, injection into the spleen, or administration under the renal capsule of fetal liver. Cells may be administered in one infusion, or through successive infusions over a defined time period sufficient to generate a therapeutic effect. Exemplary methods for transplantation, engraftment assessment, and marker phenotyping analysis of transplanted transduced HSC lineage cells are well known in the art (see, for example, Pearson et al. (2008) *Curr. Protocol. Immunol.* 81:15.21.1-15.21.21; Ito et al. (2002) *Blood* 100:3175-3182; Traggiai et al. (2004) *Science* 304:104-107; Ishikawa et al. *Blood* (2005) 106:1565-1573; Shultz et al. (2005) *J. Immunol.* 174:6477-6489; and Holyoake et al. (1999) *Exp. Hematol.* 27:1418-1427).

The number of transduced HSC lineage cells transduced may be adjusted based on the desired level of engraftment. Generally, $1 \times 10^5$ to about $1 \times 10^9$ cells/kg of body weight, from about $1 \times 10^6$ to about $1 \times 10^8$ cells/kg of body weight, or about $1 \times 10^7$ cells/kg of body weight, or more cells, as necessary, may be transplanted. Transplantation of at least about $1.0 \times 10^6$, $2.0 \times 10^6$, $3.0 \times 10^6$, $4.0 \times 10^6$, or $5.0 \times 10^6$ per kg of incubator host is also generally effective (see, for example, Olivieri et al. (1998) *Haematologica* 83:329-337; Mavroudis et al. (1996) *Blood Vo.* 88:3223-3229; Singhal et al. (2000) *Bone Marrow Transplant.* 26:489-96; and Bittencourt et al. (2002) *Blood* 99:2726-2733).

Engraftment of transplanted transduced HSC lineage cells may be assessed by any of various methods, such as, but not limited to, flow cytometric analysis of cells of interest obtained from the incubator animals at one or more time points following transplantation. For example, the number of colony forming cells, the number of granulocyte-macrophage colony forming cells, the number of burst forming unit-erythroid cells, the number of colony forming unit-granulocyte erythroid monocyte macrophage cells, that are collected or administered, may be analyzed. "Engraftment" is successful where transplanted transduced HSC lineage cells and cells differentiated therefrom in the incubator animal are detected at a time when the majority of any transplanted non-HSC lineage cells has degenerated. Serial transfer of cells into a secondary recipient and engraftment thereof is a further test of engraftment in the primary incubator animal. In one embodiment, the engraftment level of transplanted transduced HSC lineage cells may be calculated as the percentage of transplanted transduced HSC lineage cells as assessed by analysis of a phenotypic marker relative to the total numbers of cells expressing the marker, such as in a population of cells from bone marrow, peripheral blood, etc. The engraftment level is generally 70% or more, preferably 80% or more, more preferably 90% or more, particularly preferably 95% or more. The engraftment level of transplanted transduced HSC lineage cells in spleen is generally 70% or more, preferably 80% or more, more preferably 85% or more, more preferably 90% or more. The engraftment level of transplanted transduced HSC lineage cells in peripheral blood is generally 60% or more, preferably 70% or more, more preferably 80% or more. Engraftment may be detected by flow cytometry as 0.05% or greater transplanted cells in the blood, spleen or bone marrow at 10-12 weeks after transplantation.

After transplantation and engraftment, transduced HSC cell lineage populations and progeny thereof may be obtained, isolated, and/or purified using methods described above. At any time, engrafted cells may be analyzed by marker phenotyping, gene expression analyses, reporter activity, and the like to determine the cell state of the cells. In one embodiment, resting reconstituted immune cells of interest are selected, such as any of the HSC lineage cell types described above. "Resting" cells refer to a non-cycling cell in a non-replicative state. Although resting cells may have the ability to replicate and divide upon activation, they are quiescent since they are non-cycling. Thus, "resting" cells are not simply manipulated immune cells that have been stimulated to divide and then engineered to revert to a quiescent, non-dividing phase.

In one embodiment, the resting cells are naive. "Naive" cells are immune cells that have differentiated in bone marrow, successfully undergone positive and negative selection in the thymus, and are mature, but have not been activated and are not memory cells. Naive T cells are commonly characterized by the surface expression of L-selectin (CD62L); the absence of the activation markers, CD25, CD44, or CD69; and the absence of memory CD45RO isoform. They also express functional IL-7 receptors, consisting of subunits IL-7 receptor-α, CD127, and common-γ chain, CD132. In the naive state, T cells are thought to be quiescent and non-dividing, requiring the common-gamma chain cytokines IL-7 and IL-15 for homeostatic survival mechanisms. By contrast, activated T cells express or upregulate expression of surface markers, CD25, CD44, CD62L$^{low}$, and CD69 and may further differentiate into memory T cells. Naive B cells have not been exposed to antigen since they would either become a memory B cell or a plasma cell that secretes antibodies. In one embodiment, a resting cell becomes "activated" when it is triggered to enter into a state of reproduction or doubling and may include a cell entering the cell cycle, cell division, or mitosis. In another embodiment, a resting cell may also become "activated" when it encounters an external signal, such as an antigen or a cytokine, that initiates the activity of terminally differentiated, mature immunological cells to generate an immune response (e.g., T cell or B cell function).

D. Uses of Transduced HSC Lineage Cells

The methods described herein for generating transduced HSC lineage cells that are differentiated in vivo, as well as progeny thereof and compositions thereof. Such compositions have various utilities such as, but not limited to, as models of growth and differentiation of immune cells, in vivo study of immune response, and for the testing of agents (e.g., gene products and compounds) affecting hematopoietic and immune cell function. The preservation of biologically faithful immune cell development allows for the embodiments of the present invention to be useful for analyzing various autoimmune, allergic (e.g., asthma, atopic dermatitis, allergic conjunctivitis, pollen allergy, food allergy, etc.), vaccination, immunotolerance, cancer immunotherapy, immune exhaustion, immunological memory, or immunological epitope responses. Such compositions can also be used for prognostic, diagnostic, and therapeutic purposes as described herein.

Methods of analyzing such responses may use cell populations selected from the incubator animals in vitro or upon additional transplantation into an experimental animal. An "experimental animal" is an animal in which transduced cell types of interest are transplanted and exogenous perturbations are made in order to analyze the effects on or achieved through the transplanted transduced cell types. Experimental animals and transplantation methods may follow any or all of the criteria described for incubator animals above. For assays in which a gene of interest is expressed from HSC cells are inducibly expressed, transcriptional and/or translational induction may be achieved before, simultaneously with, or after, the exogenous perturbation according to well-known methods in the art described above.

a) Screening Methods

One aspect of the present invention relates to methods of selecting agents (e.g., nucleic acids, proteins, antibodies, fusion proteins, peptides, or small molecules) which modulate an immune response. Such methods utilize screening assays using cell based assays either in vitro, ex vivo, or in vivo. The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages. Immune responses encompass assays testing autoimmune, allergic, vaccination, immunotolerance, cancer immunotherapy, immune exhaustion, immunological memory, or immunological epitope responses. The test agent may be analyzed to determine whether it improves a response, condition, or symptom of interest. For example, a test agent that induces differentiation of cells, such as stem cells or terminally differentiated cells will be identified as an agent that induces differentiation of cells.

In some embodiments, the screening methods of the present invention are adapted for high-throughput analysis. For example, methods for preparing a combinatorial library of molecules that may be tested for a desired activity are well known in the art and include, for example, methods of making a phage display library of peptides, which may be constrained peptides (see, for example, U.S. Pat. Nos. 5,622,699 and 5,206,347; Scott and Smith (1992) *Science* 249: 386-390; and Markland et al. (1991) *Gene* 109:13-19); a peptide library (see, for example, U.S. Pat. No. 5,264,563); a peptidomimetic library (see, for example, Blondelle et al. (1995) *Trends Anal. Chem.* 14:83-92; a nucleic acid library (see, for example, O'Connell et al. (1996) *Proc. Natl. Acad. Sci. U.S.A.* 93:5883-5887; and Tuerk and Gold (1990) *Science* 249:505-510; Gold et al. (1995) *Ann. Rev. Biochem.* 64:763-797); an oligosaccharide library (see, for example, York et al. (1996) *Carb. Res.* 285:99-128; Liang et al. (1996) *Science* 274:1520-1522; and Ding et al. (1995) *Adv. Expt. Med. Biol.* 376:261-269); a lipoprotein library (see, for example, de Kruif et al. (1996) *FEBS Lett.* 399:232-236); a glycoprotein or glycolipid library (see, for example, Karaoglu et al. (1995) *J. Cell Biol.* 130:567-577); or a chemical library containing, for example, drugs or other pharmaceutical agents (see, for example, Gordon et al. (1994) *J. Med. Chem.* 37:1385-1401 and Ecker and Crooke (1995) *BioTechnol.* 13:351-60).

For a high throughput format, cells of interest may be introduced into wells of a multiwell plate or of a glass slide or microchip, and may be contacted with the test agent. Generally, the cells are organized in an array, particularly an addressable array, such that robotics conveniently may be used for manipulating the cells and solutions and for monitoring the cells of the invention, particularly with respect to the function being examined. An advantage of using a high-throughput format is that a number of test agents may be examined in parallel, and if desired, control reactions also may be run under identical conditions as the test conditions. As such, the methods of the present invention provide a means to screen one, a few, or a large number of test agents in order to identify an agent that may alter a function of desired cells.

In one embodiment, the invention relates to assays for screening agents that bind to, or modulate the expression and/or activity of an immune-related biomolecule in the context of HSC lineage cells expressing a gene of interest described above. In one embodiment, a method for identifying an agent to modulate an immune response entails determining the ability of the agent to modulate, e.g., enhance or inhibit, the interaction between immune-related biomolecules in the context of HSC lineage cells expressing a gene of interest. Such agents include, without limitation, antibodies, proteins, fusion proteins, small molecules, and nucleic acids.

Modulation of an immune response may be determined using standard methods in the art, including, for example, (1) increased or decreased copy number (e.g., by FISH, FISH plus SKY, single-molecule sequencing, e.g., as described in the art at least at J. Biotechnol., 86:289-301, or qPCR), overexpression or underexpression of a nucleic acid (e.g., by ISH, Northern Blot, or qPCR), increased or decreased biomarker protein (e.g., by IHC) and/or biomarker metabolite, or increased or decreased activity (determined by, for example, analyzing modulation of direct protein function or downstream effects thereof; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human; (3) its absolute or relatively modulated presence or absence in clinical subset of patients such as those having defined or undefined genetic backgrounds.

For example, methods of evaluating the copy number of a biomarker locus include, but are not limited to, hybridization-based assays. Hybridization-based assays include, but are not limited to, traditional "direct probe" methods, such as Southern blots, in sir hybridization (e.g., FISH and FISH plus SKY) methods, and "comparative probe" methods, such as comparative genomic hybridization (CGH), e.g., cDNA-based or oligonucleotide-based CGH. The methods may be used in a wide variety of formats including, but not limited to, substrate (e.g. membrane or glass) bound methods or array-based approaches. Other suitable amplification methods include, but are not limited to, ligase chain reaction (LCR) (see Wu and Wallace (1989) *Genomics* 4: 560, Landegren, et al. (1988) *Science* 241:1077, and Barringer e al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc. Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

Expression of immune-related biomolecules may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods. In preferred embodiments, activity of a particular gene is characterized by a measure of gene transcript (e.g. mRNA), by a measure of the quantity of translated protein, or by a measure of gene product activity. Marker expression may be monitored in a variety of ways, including by detecting mRNA levels, protein levels, or protein activity, any of which may be measured using standard techniques. Detection may involve quantification of the level of gene expression (e.g., genomic DNA, cDNA, mRNA, protein, or enzyme activity), or, alternatively, may be a qualitative assessment of the level of gene expression, in particular in comparison with a control level. The type of level being detected will be clear from the context. Various amplification and detection methods may also be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR), real time PCR, NASBA, Q-beta amplification, target-mediated amplification, ligase chain reaction, self-sustained sequence replication (SSR), transcription amplification, and the like. Many techniques are known in the state of the art for determining absolute and relative levels of gene expression, commonly used techniques suitable for use in the present invention include in situ hybridization, microarray, chip array, serial analysis of gene expression (SAGE), Northern analysis. RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

The activity or level of an immune-related biomolecule polypeptide may be detected and/or quantified by detecting or quantifying the expressed polypeptide. The polypeptide may be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-immune checkpoint inhibitor therapy. Any method known in the art for detecting polypeptides may be used. Such methods include, but are not limited to, immunodiffusion, immunoelectrophoresis, radioimmunoassay (RIA), enzyme-linked immunosorbent assays (ELISAs), immunofluorescent assays. Western blotting, binder-ligand assays, immunohistochemical techniques, agglutination, complement assays, high performance liquid chromatography (HPLC), thin layer chromatography (TLC), hyperdiffusion chromatography, and the like (e.g., "Basic and Clinical Immunology", Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

In one embodiment, a method for identifying an agent which promotes an immune response entails determining the ability of the candidate agent to promote or inhibit the interaction of immune-related biomolecule in the context of HSC cells expressing a gene of interest.

In another embodiment, a method for identifying an agent which inhibits an immune response entails determining the ability of the candidate agent to promote or inhibit the interaction of immune-related biomolecule in the context of HSC cells expressing a gene of interest.

The assays are cell-based assays and may comprise, for example, contacting (a) an HSC cell expressing a gene of interest, with a test agent and determining the ability of the test agent to modulate (e.g. stimulate or inhibit) the interaction between immune-related biomolecules (e.g., polypeptides) of interest. Determining the ability of the polypeptides to bind to, or interact with, each other may be accomplished, e.g., by measuring direct binding or by measuring a parameter of immune cell response.

For example, in a direct binding assay, polypeptides may be coupled with a radioisotope or enzymatic label such that binding of immune-related biomolecules may be determined by detecting the labeled protein in a complex. For example, the polypeptides may be labeled with $^{125}I$, $^{35}S$, $^{14}C$, or $^{3}H$, either directly or indirectly, and the radioisotope detected by direct counting of radioemission or by scintillation counting. Alternatively, the polypeptides may be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between immune-related biomolecules of interest without the labeling of any of the interactants. For example, a microphysiometer may be used to detect the interaction of immune-related biomolecule polypeptides without the labeling of either polypeptide (McConnell et al. (1992) *Science* 257: 1906-1912). As used herein, a "microphysiometer" (e.g., Cytosensor) is an analytical instrument that measures the rate at which a cell acidifies its environment using a light-addressable potentiometric sensor (LAPS). Changes in this acidification rate may be used as an indicator of the interaction between compound and receptor.

In a preferred embodiment, determining the ability of the test agents (e.g. nucleic acids, polypeptides, antibodies, fusion proteins, peptides, or small molecules) to antagonize the interaction between a given set of immune-related biomolecules may be accomplished by determining the activity of one or more members of a set of immune-related biomolecule polypeptides. For example, the activity of polypeptides may be determined by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the polypeptides, such as various autoimmune, allergic (e.g., asthma, atopic dermatitis, allergic conjunctivitis, pollen allergy, food allergy, etc.), vaccination, immunotolerance, cancer immunotherapy, immune exhaustion, immunological memory, or immunological epitope responses. Determining the ability of the test agent to bind to or interact with said polypeptide may be accomplished, for example, by measuring the ability of a compound to modulate immune cell costimulation or inhibition in a proliferation assay, or by interfering with the ability of said polypeptide to bind to antibodies that recognize a portion thereof.

Test agents that inhibit immune responses may be identified by their ability to inhibit immune cell proliferation, and/or effector function, or to induce anergy, clonal deletion, and/or exhaustion when added to an assay. For example, cells may be cultured in the presence of an agent that stimulates signal transduction via an activating receptor. A number of recognized readouts of cell activation may be employed to measure cell proliferation or effector function (e.g., antibody production, cytokine production, phagocytosis) in the presence of the activating agent. The ability of a test agent to block this activation may be readily determined by measuring the ability of the agent to effect a decrease in proliferation or effector function being measured, using techniques known in the art.

For example, agents of this invention may be tested for the ability to inhibit or enhance costimulation in a T cell assay, as described in Freeman et al. (2000) *J. Exp. Med.* 192:1027 and Latchman e al. (2001) *Nat. Immunol.* 2:261. HSC cells expressing a gene of interest may be CD4+ T cells or, alternatively, CD4+ T cells may be isolated from human PBMCs and stimulated with activating anti-CD3 antibody. Proliferation of T cells may be measured by $^{3}H$ thymidine incorporation. An assay may be performed with or without CD28 costimulation in the assay. Similar assays may be performed with Jurkat T cells and PHA-blasts from PBMCs.

Alternatively, agents of the present invention may be tested for the ability to modulate cellular production of cytokines which are produced by or whose production is enhanced or inhibited in immune cells in response to immune response modulation. For example, HSC cells expressing a gene of interest may be suboptimally stimulated in vitro with a primary activation signal. For example, T cells may be stimulated with phorbol ester, anti-CD3 antibody or preferably antigen in association with an MHC class II molecule, and given a costimulatory signal, e.g., by a stimulatory form of B7 family antigen, for instance by a cell transfected with nucleic acid encoding a B7 polypeptide and expressing the peptide on its surface or by a soluble, stimulatory form of the peptide. Known cytokines released into the media may be identified by ELISA or by the ability of an antibody which blocks the cytokine to inhibit immune cell proliferation or proliferation of other cell types that is induced by the cytokine. For example, an IL-4 ELISA kit is available from Genzyme (Cambridge Mass.), as is an IL-7 blocking antibody. Blocking antibodies against IL-9 and IL-12 are available from Genetics Institute (Cambridge, Mass.). The effect of stimulating or blocking the interaction of immune-related biomolecules on the cytokine profile may then be determined. To identify cytokines which may play a role the induction of tolerance, an in vitro T cell costimulation assay as described above may be used. In this case, T cells would be given the primary activation signal and contacted with a selected cytokine, but would not be given the costimulatory signal. After washing and resting the immune cells, the cells would be rechallenged with both a primary activation signal and a costimulatory signal. If the immune cells do not respond (e.g., proliferate or produce cytokines) they have become tolerized and the cytokine has not prevented the induction of tolerance. However, if the immune cells respond, induction of tolerance has been prevented by the cytokine. Those cytokines which are capable of preventing the induction of tolerance may be targeted for blockage in vivo in conjunction with reagents which block B lymphocyte antigens as a more efficient means to induce tolerance in transplant recipients or subjects with autoimmune diseases.

In one or more embodiments of the above described assay methods, it may be desirable to immobilize either polypeptides to facilitate separation of complexed from uncomplexed forms of one or both of the proteins, as well as to accommodate automation of the assay. Binding of a test compound to a polypeptide, may be accomplished in any vessel suitable for containing the reactants. Examples of such vessels include microtiter plates, test tubes, and microcentrifuge tubes. In one embodiment, a fusion protein may be provided which adds a domain that allows one or both of the proteins to be bound to a matrix. For example, glutathione-S-transferase/immune-related polypeptide fusion proteins, or glutathione-S-transferase/target fusion proteins, may be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes may be dissociated from the matrix, and the level of polypeptide binding or activity determined using standard techniques.

In an alternative embodiment, determining the ability of the test compound to modulate the activity of an immune-related polypeptide of interest may be accomplished as described above for cell-based assays, such as by determining the ability of the test compound to modulate the activity of a polypeptide that functions downstream of the polypeptide. For example, levels of second messengers may be determined, the activity of the interactor polypeptide on an appropriate target may be determined, or the binding of the interactor to an appropriate target may be determined as previously described.

In some embodiments, determination as to modulation of an immune-related indication of interest may be made in comparison to a control. The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels may be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient may be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

As described above, control and experimental assays may involve the use of samples. The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the amount or expression of at least one marker in the sample. Samples are typically from a diseased tissue, such as cancer cells or tissues. The control sample may be from the same subject or from a different subject. The control sample is typically a normal, non-diseased sample. However, in some embodiments, such as for staging of disease or for evaluating the efficacy of treatment, the control sample may be from a diseased tissue. The control sample may be a combination of samples from several different subjects.

Comparison to a control may distinguish between the "normal" level of expression or activity of an immune-related biomarker and that which is modulated. An "overexpression" or "significantly higher level" of expression or activity refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level in a control sample and preferably, the average expression level of the biomarker in several control samples. A "significantly lower level" of expression or activity refers to an expression level or activity in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level or activity in a control sample and preferably, the average expression level of the biomarker in several control samples.

This invention further pertains to novel agents identified by the above-described screening assays. Accordingly, it is within the scope of this invention to further use an agent identified as described herein in an appropriate animal model. For example, an agent identified as described herein may be used in an animal model to determine the efficacy, toxicity, or side effects of treatment with such an agent. Alternatively, an agent identified as described herein may be used in an animal model to determine the mechanism of action of such an agent. Furthermore, this invention pertains to uses of novel agents identified by the above-described screening assays for treatments as described herein.

b) Therapeutic Methods

In one aspect, the present invention provides a method for modulating or preventing in a subject, a disease or condition associated with an unwanted or undesirable immune responses, such as overactive or underactive immune responses. In another aspect, the present invention provides a method for preventing in a subject, a disease or condition associated with an unwanted or less than desirable immune response. The term "subject" refers to a) any healthy animal, such as a mammal or human; b) any animal, such as a mammal or human, afflicted with a immune-related disorder of interest; or c) any animal as described above from which HSC cells expressing a gene of interest is expressed are expressed. Subjects at risk for a disease that would benefit from treatment with the claimed agents or methods may be identified, for example, by any or a combination of diagnostic or prognostic assays known in the art. Administration of a prophylactic agent may occur prior to the manifestation of symptoms associated with an unwanted or less than desirable immune response. The appropriate agent used for treatment (e.g. antibodies, peptides, fusion proteins or small molecules) may be determined based on clinical indications and may be identified, e.g., using screening assays described herein.

Another aspect of the invention pertains to therapeutic methods of modulating an immune response, e.g., by modulating the interaction between immune-related biomolecules a) within an HSC expressing a gene of interest, b) between such an HSC and another cell, or c) between cells other than the HSC expressing a gene of interest. Without being bound by theory, it is believed that engineered HSC expressing a gene of interest described herein faithfully reproduce in vivo-generated, normal HSC lineage cells to thereby produce more physiologically relevant responses relative to other methods of HSC cell engineering.

Modulatory methods of the present invention involve contacting a cell and/or an HSC expressing a gene of interest with an agent that modulates the interaction between immune-related biomolecules. Exemplary agents that modulate the interaction between immune-related biomolecules have been described above. For example, an agent that modulates immune-related biomolecule polypeptide activity includes a nucleic acid or a protein molecule, a naturally-occurring target molecule of the immune-related biomolecule protein, an anti-immune-related biomolecule protein antibody, immune-related biomolecule protein agonists or antagonists (e.g., antisense nucleic acid molecule, triplex oligonucleotide, and ribozymes), a peptidomimetic of an immune-related biomolecule protein agonist or antagonist, nucleic acid agonists or antagonists of immune-related biomolecule protein expression or activity, or other small molecule.

These modulatory agents may be administered in vitro or ex vivo (e.g., by contacting the cell with the agent) or, alternatively, in vivo (e.g., by administering the agent to a subject). As such, the present invention relates to methods of treating an individual afflicted with a disease or disorder that would benefit from modulation of an immune response.

There are numerous embodiments of the invention for downregulating immune responses. Downregulation may be in the form of inhibiting or blocking an immune response already in progress, or may involve preventing the induction of an immune response. The functions of activated immune cells may be inhibited by down-regulating immune cell responses, or by inducing specific anergy in immune cells, or both.

In one embodiment of the invention, tolerance is induced against specific antigens by co-administering an antigen with an agent (e.g. antibody, peptide, fusion protein, or small molecule) that modulates the interaction between immune-related polypeptides. For example, tolerance may be induced to specific proteins. In one embodiment, immune responses to allergens (e.g., food allergens), or to foreign proteins to which an immune response is undesirable, may be inhibited. In similar manners, reduced clonal deletion and/or increased exhaustion (e.g., T cell exhaustion) may be induced.

In another embodiment, treatment methods may further use combinations of additional agents. For example, agents that block an activity of costimulatory pathways, such as that of other B lymphocyte antigen like B7-1, B7-2, or B7-3) may be used to further downmodulate immune responses. Two separate agents that downmodulate immune responses may be combined as a single composition or administered separately (simultaneously or sequentially) to more effectively downregulate immune cell mediated immune responses in a subject. Furthermore, a therapeutically active amount of one or more of the subject agents, may be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs, (e.g., rapamycin, cyclosporine A or FK506).

Downregulating immune responses is useful for treating a number of conditions, e.g., in situations of tissue, skin and organ transplantation, in graft-versus-host disease (GVHD), or in autoimmune diseases such as systemic lupus erythematosus, multiple sclerosis, allergy, a transplant, hypersensitivity response, a disorder requiring increased CD4+ T cell production or function, a disorder requiring improved vaccination efficiency, a disorder requiring increased regulatory T cell production or function, and a disorder requiring improved vaccination efficiency. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation may promote the generation of an inhibitory signal. Moreover, inhibition may also be sufficient to anergize the immune cells, thereby inducing tolerance in a subject. Induction of long-term tolerance avoids the necessity of repeated administration of these blocking reagents.

Downmodulation of immune responses are also useful in treating autoimmune disease. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, agents that promote an inhibitory function mediated by the interaction between immune-related biomolecules of interest may induce antigen-specific tolerance of autoreactive immune cells, which could lead to long-term relief from the disease. The efficacy of reagents in preventing or alleviating autoimmune disorders may be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see. e.g., Paul ed., *Fundamental Immunology*, Raven Press, New York, Third Edition 1993, chapter 30).

Inhibition of immune cell activation is also useful therapeutically in the treatment of allergy and allergic reactions, e.g., by inhibiting IgE production. Allergic reactions may be systemic or local in nature, depending on the route of entry of the allergen and the pattern of deposition of IgE on mast cells or basophils. Thus, inhibition of immune cell mediated allergic responses (e.g., to food) locally or systemically by administration of an agent described herein that promotes an inhibitory function mediated by immune-related biomolecules of interest.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus may be treated with agents that modulate these interactions.

Downregulation of an immune response by modulating the interaction between immune-related biomolecules of interest may also be useful in treating an autoimmune attack of autologous tissues. It is therefore within the scope of the invention to modulate conditions exacerbated by autoimmune attack, such as autoimmune disorders, as well as conditions such as heart disease, myocardial infarction, and atherosclerosis.

In other embodiments, agents described herein may also be used to upregulate immune responses. In one embodiment, blockage of the interaction between immune-related biomolecules of interest results in upregulation of an immune response. Upregulation of immune responses may be in the form of enhancing an existing immune response or eliciting an initial immune response. For instance, enhancing an immune response using the subject compositions and methods is useful in treating cancer, an infectious disease (e.g., bacteria, viruses, or parasites), a parasitic infection, asthma associated with impaired airway tolerance, a neurological disease, and an immunosuppressive disease.

Exemplary infectious disorders include viral skin diseases, such as Herpes or shingles, in which case such an agent may be delivered topically to the skin. In addition, systemic viral diseases, such as influenza, the common cold, and encephalitis might be alleviated by systemic administration of such agents. In one preferred embodiment, agents that upregulate the immune response described herein are useful for modulating the arginase/iNOS balance during *Trypanosoma cruzi* infection in order to facilitate a protective immune response against the parasite.

Alternatively, immune responses may be enhanced in an infected patient through an ex vivo approach, for instance, by removing immune cells from the patient, contacting immune cells in vitro with an agent that modulate the interaction between immune-related biomolecules of interest and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response.

Agents that upregulate an immune response may be used prophylactically in vaccines against various polypeptides (e.g., polypeptides derived from pathogens). Immunity against a pathogen (e.g., a virus) may be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response may be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens may be induced by administering appropriate agents described herein that upregulate the immune response. In one embodiment, an autologous antigen, such as a tumor-specific antigen, may be coadministered. In another embodiment, an immune response may be stimulated against an antigen (e.g., an autologous antigen) to treat a neurological disorder. In another embodiment, the subject agents may be used as adjuvants to boost responses to foreign antigens in the process of active immunization.

In one embodiment, immune cells are obtained from a subject and cultured ex vivo, in the presence of an agent as described herein, to expand the population of immune cells and/or to enhance immune cell activation. In a further embodiment the immune cells are then administered to a subject. Immune cells may be stimulated in vitro by, for example, providing to the immune cells a primary activation signal and a costimulatory signal, as is known in the art. Various agents may also be used to costimulate proliferation of immune cells. In one embodiment immune cells are cultured ex vivo according to the method described in PCT Application No. WO 94/29436. The costimulatory polypeptide may be soluble, attached to a cell membrane, or attached to a solid surface, such as a bead.

In still another embodiment, agents described herein useful for upregulating immune responses may further be linked, or operatively attached, to toxins using techniques that are known in the art, e.g., crosslinking or via recombinant DNA techniques. Such agents may result in cellular destruction of desired cells. In one embodiment, a toxin may be conjugated to an antibody, such as a bispecific antibody. Such antibodies are useful for targeting a specific cell population, e.g., using a marker found only on a certain type of cell. The preparation of immunotoxins is, in general, well known in the art (see, e.g., U.S. Pat. No. 4,340,535, and EP 44167). Numerous types of disulfide-bond containing linkers are known which may successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and Pseudomonas exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

The terms "therapeutic response" or "therapeutic responsiveness" refer to a beneficial endpoint attained when exposed to a stimulus, such as an immunomodulatory response sufficient to modulate a target immune response. The terms may also refer to an improved prognosis, for example, as reflected by an increased time to cancer recurrence, which is the period to first recurrence censoring for second primary cancer as a first event or death without evidence of recurrence, or an increased overall survival, which is the period from treatment to death from any cause. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The amount of cells needed for achieving a therapeutic effect may be determined empirically in accordance with conventional procedures for the particular purpose. Generally, for administering cells for therapeutic purposes, the cells are given at a pharmacologically effective dose. By "pharmacologically effective amount" or "pharmacologically effective dose" is an amount sufficient to produce the desired physiological effect or amount capable of achieving the desired result. Therapeutic benefit also includes halting or slowing the progression of the underlying disease or disorder, regardless of whether improvement is realized. Pharmacologically effective dose, as defined above, will also apply to therapeutic agents described herein used either alone or in combination with the cells. Effective doses of such therapeutic agents are well known in the art and may be determined by the ordinarily skilled artisan based on standard criteria, such as regulatory information, age, weight, state of health of the patient, and the nature and the severity of the indication. Suitable dosage ranges can vary according to these considerations. Moreover, the mode of administration may vary depending on such factors as well. Agents, including cells, may be introduced to the desired site by direct injection, or by any other means used in the art including, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular administration.

EXEMPLIFICATION

This invention is further illustrated by the following examples, which should not be construed as limiting.

Example 1: Materials and Methods for Examples 2-7

A. Mice

P14 TCR Tg mice were used as described in Pircher et al. (1989) *Nature* 342:559-561. Wild type C57BL/6J, Ly5.1 (CD45.1), and Thy1.1 mice were purchased from Jackson Laboratories (Bar Harbor, Me.). All mice were used according to the Harvard Medical School Standing Committee on Animals and National Institutes of Animal Healthcare Guidelines. Animal protocols were approved by the Harvard Medical School Standing Committee on Animals.

B. Generation of Bone Marrow Chimeras

Bone marrow was isolated and red blood cells lysed using ACK lysis buffer (Gibco). LSK cells were enriched using anti-CD117 microbeads (Miltenyi Biotech) and then sorted using a BD FACSAria® cytometer. Sorted cells were plated overnight in StemSpan SFEM medium (StemCell Technologies) with 100 µg/ml SCF, TPO, IL-7, Flt31 (PeproTech). Cells were then spin-infected with lentiviral supernatants at 650×g for 90 min. at 37° C. on non-treated plates that had been coated overnight at 4° C. with 100 µg/ml RetroNectin (Takara Bio). Fresh medium was added after 1 hr. and cells were rested overnight. Viral stocks were titrated to ensure the majority of cells were infected with a single virus. The cells were then washed in PBS (Gibco) and 50,000 cells were injected intravenously in recipient mice that have been irradiated with 2 doses of 600 cGy, 3 hours apart.

C. Lentivirus Production 293T cells were seeded in DMEM with 10% FBS. The following day, the cells were transfected with shRNA construct pLKO.1 or 1×LacO (available from Sigma-Aldrich as "MISSION® 1×LacO Inducible") with Pax2 (gag. pol) and VSV-G plasmids using TransIT-LTI (Mirus Bio) or ExGen 500 (Thermo Scientific Fermentas). Viral supernatants were collected 48-72 hrs. later.

D. In Vitro Knockdown of GFP

A stable GFP-expressing Jurkat cell line was constructed by cloning GFP+ cells following transduction with PGK-eGFP lentivirus. GFP-Jurkat cells were transduced with shRNA targeting GFP under a constitutive (pLKO.1) or inducible (1 xLacO) promoters. Varying doses of dioxane-free IPTG (Promega) were added at the indicated concentrations and durations.

E. T Cell Transfers and Infections

CD8$^+$ T cells from bone marrow chimeric animals were isolated using the CD8$^+$ T cell isolation kit II for magnetic separation (Miltenyi Biotech) and then GFP$^+$ CD8$^+$ congenic cells were sorted using BD FACSAria cytometer. P14 CD8$^+$ T cells (10-10$^6$ cell/animal) were injected in recipient mice intravenously (i.v.), which were subsequently infected intraperitoneally (i.p.) with 2×10$^5$ p.f.u. LCMV Armstrong. For influenza infections, the mice were anesthetized with 2.5% Avertin and infected with 0.5 LD$_{50}$ H1N1 Influenza virus (PR8), engineered to express GP$_{33-41}$ peptide of LCMV (PR8-GP33)[35], intranasally. Both viruses were a generous gift of Dr. E. John Wherry (University of Pennsylvania School of Medicine, Philadelphia, Pa.).

F. Flow Cytometry and Cell Sorting

Spleen or bone marrow tissue was harvested, homogenized into single cell suspension, and resuspended in staining buffer (2 mM EDTA and 1% FBS in PBS; Gibco) together with combinations of the following antibodies: anti-CD8a (53-6.7), anti-CD4 (RM4-5), anti-B220 (RA3-6B2), anti-CD11b (M1/70), anti-CD11c (N418), anti-CD44 (IM7), anti-CD62L (MEL-14), anti-CD45.1 (A20), anti-CD45.2 (104), anti-Thy1.1 (OX-7), anti-Thy1.2 (30-H12), anti-CD25 (PC61), anti-CD122 (TM-β1), anti-CD127 (A7R34), anti-CXCR3 (CXCR3-173) (all BioLegend), and anti-Ki-67 (B56, BD Biosciences). Poly-caspase activity was detected using FLICA Vybrant-FAM Assay Kit (Life Technologies).

To assess T cell proliferation, mice were injected with 2 mg BrdU i.p. 16 hrs. prior to analysis and BrdU incorporation was detected using the FITC BrdU Flow Kit (BD Pharmingen). LSK cells were sorted from CD117-enriched bone marrow cells stained with CD117 (ACK2). Sca-1 (D7) and lineage antibody cocktail which included biotin labeled anti-CD5 (53-7.3), anti-Gr1 (RB6-8C5), anti-B220 (RA3-6B2), anti-CD3e (145-2C11), anti-CD11b (M1/70), anti-Ter-119 (Ter-119). Data were acquired using LSR II or Accuri C6 (BD Biosciences) cytometers and analyzed with FlowJo software (v9.7.2, TreeStar).

G. shRNA Construct Generation

Target sequences of the shRNA used include: shBatf 1 (CCGCAAAGAGATCAAACAGCT), shBatf 2 (CTGGACAAGTATTGAACACAA), shBatf 3 (GAGCTCAAGTACTTCACATCA), shLacZ (CCGTCATAGCGATAAC-GAGTT), shRFP (GCTTCAAGTGGGAGCGCGTGA), shGFP (ACAACAGCCACAACGTCTATA). Cloning methods were performed according to standard methods available on the World Wide Web at broadinstitute.org/rnai.public/. Briefly, complementary oligos (IDT) were annealed and ligated into AgeI and EcoRI digested pLKO.1 and 1×LacO (all obtained from The RNAi Consortium, Broad Institute). All ligated constructs were sequence verified for the presence of the correct shRNA by Sanger sequencing.

Example 2: Lentivirus-Transduced Stem Cells Reconstitute Blood Immune Lineages and Give Rise to Effector CDI Effector T Cells with Unaltered Functionality Resting T cells are refractory to lentiviral transduction, but hematopoietic stem cells (HSC) are readily transduced. Thus, bone marrow chimeric animals were generated using transduced HSCs in which the hematopoietic lineages (including T cells) would be reconstituted with transduced cells (FIG. 1A). Lineage$^-$/c-kit$^+$/sca-1$^+$ (LSK) cells (which include HSC and multipotent progenitors) were isolated from the bone marrow of P14 TCR transgenic mice in which all CD8$^+$ T cells express a TCR specific for LCMV GP$_{33-41}$ peptide presented on H-2Db (FIG. 1A). The cells were transduced with a lentivirus carrying a GFP expression cassette so that the fate of transduced cells could be tracked. Congenic markers were used to distinguish transplanted cells from recipient cells in bone marrow chimeras.

In order to first test whether lentivirus-transduced LSK cells could be used to generate fully functional CD8$^+$ T cells, the LSK cells were transduced with lentivirus encoding GFP and the transduced cells were transplanted into lethally irradiated animals (50,000 cells/animal). Following reconstitution (8-12 weeks later), analysis of major lineages in the immune system showed that the frequency of GFP$^+$ B cells (B220$^+$), CD4$^+$ and CD8$^+$ T cells, dendritic cells (CD11c$^+$), and monocytes (CD11b$^+$) was similar to that of the LSK inoculum (FIG. 1B), indicating efficient engraftment of transduced cells. T, B and myeloid lineages developed from transplanted GFP$^+$ (transduced) and GFP (untransduced) LSK with equal efficiency (FIG. 1C).

Effector CD8$^+$ T cell function of naive CD8$^+$ T cells derived from transplanted transduced and untransduced LSK cells were assessed. Equal ratios of GFP$^+$ and GFP$^-$ naive P14 CD8$^+$ T cells were transferred to naive wild-type recipients (10,000 cells/animal) and the recipients were infected with PR8-GP33 influenza (FIG. 1D). Equal expansion and persistence of GFP$^+$ and GFP$^-$ effector CDK8$^+$ T cells at 10 days after infection was found. Thus, lentiviral transduction of LSK does not impair the development of lymphoid and myeloid lineages following transplant or alter effector CD8$^+$ T cell proliferative capacity following transfer of naive GFP$^+$ CD8$^+$ T cells.

Example 3: Naive T Cells that Develop from Transduced LSK are Indistinguishable from Wild-Type Naive T Cells It was examined whether naive CD8$^+$ T cells that developed from transduced LSK cells showed any alteration of surface phenotype, proliferation status, or gene expression that might obscure analysis of early differentiation events. Naive CD8$^+$ T cells from transduced LSK cells were compared with wild-type P14 CD8$^+$ T cells, and, as controls, P14 CD8$^+$ T cells cultured in conditions used in previous studies to facilitate direct viral transduction of T cells were also studied (Joshi et al. (2007) *Immumity* 27:281-295; Yang et al. (2012) *J. Exp. Med.* 209:1655-1670; Araki et al. (2009) *Nature* 460:108-112; Zhou et al. (2014) *Nature* 506:52-57).

Figure 2:
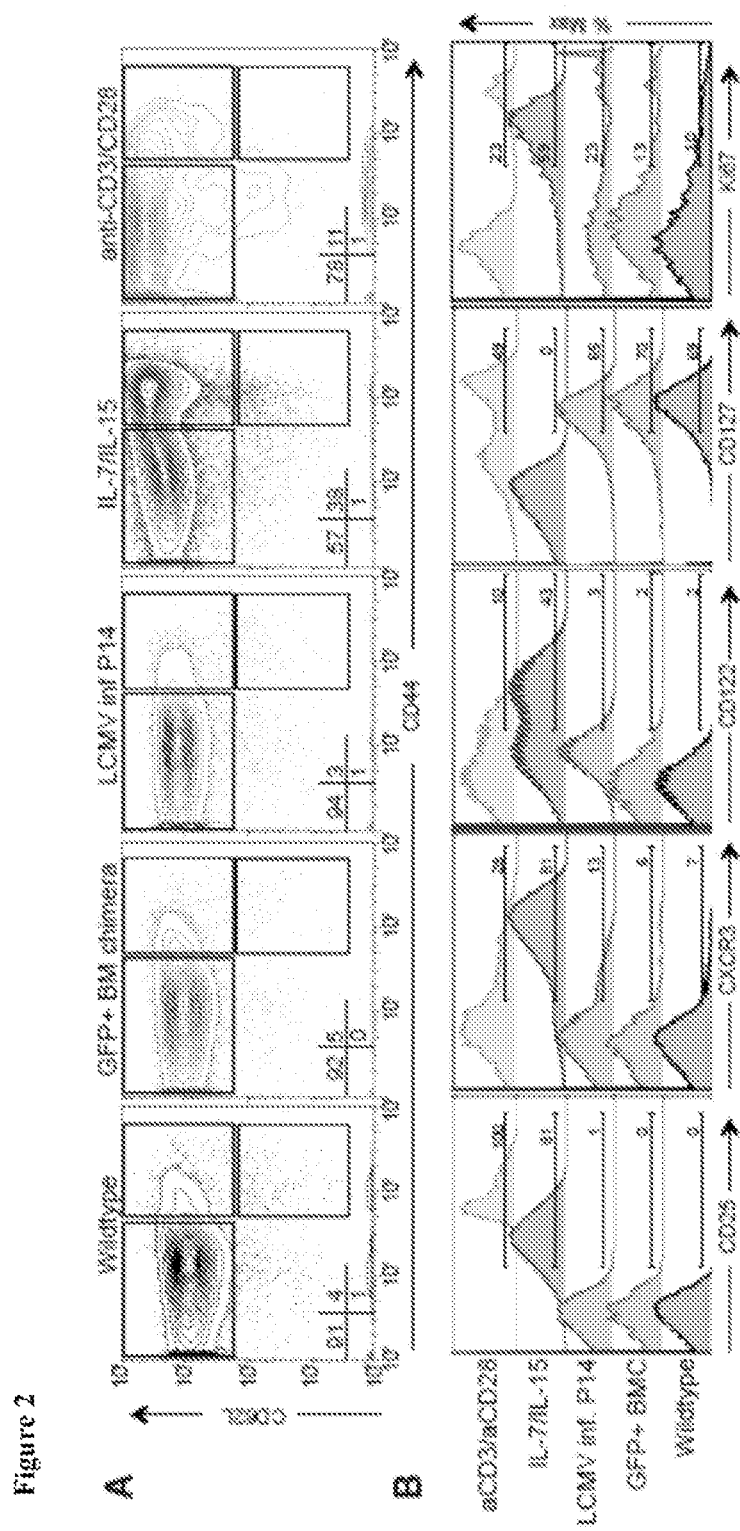
FIG. 2 includes 4 panels, identified as panels A, B, C, and D, which show that CD8$^+$ T cells derived from transduced LSK cells are indistinguishable from untransduced naive CD8$^+$ T cells. Expression of naive surface markers (Panel A) and effector molecules (Panel B) by wild-type naive P14 CD8$^+$ T cells (black); naive P14 CD8$^+$ T cells derived from transduced LSKs (GFP+BMC; naive P14 CD8$^+$ T cells stimulated by LCMV infection (LCMV inf. P14); cytokines (IL-2/IL-15); or anti-CD3 plus anti-CD28 antibodies (aCD3/aCD28) are shown. Panel C shows transcript abundance of transcriptional regulators and effector molecules changes measured by quantitative RT-PCR. Panel D shows the percentage of various immune cells differentiated from transplanted LSK cells in recipient mice.
Figure 2:
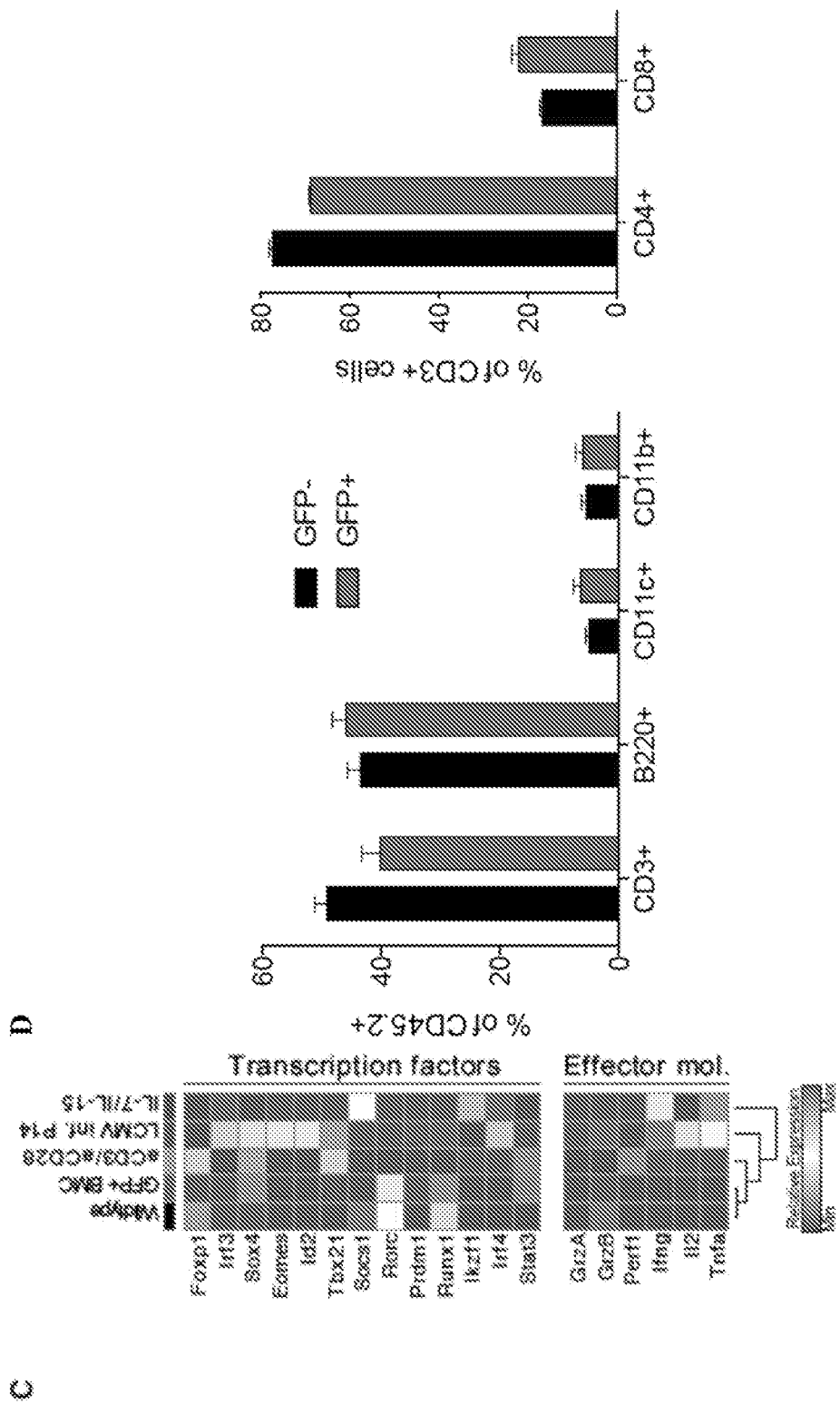

Naive T cells can be identified by expression of CD62L and lack of CD44 expression. The proportion of naive (CD62L$^+$ CD44$^-$), central memory (CD62L$^+$ CD44$^+$), and effector memory (CD62L$^-$ CD44$^+$) states was similar in the GFP$^+$ naive CD8$^+$ T cells and the ex vivo P14 stimulation, but differed in other stimulation conditions, particularly with cytokine treatment (FIG. 2A). The expression of genes characteristic of effector differentiation including CD25, CXCR3, CD127, CD122 was not different in GFP$^+$ naive cells, but was altered in naive T cells treated with anti-CD3/CD28 or cytokines. Proliferation was measured by Ki-67 staining and it was found that GFP$^+$ naive CD8$^+$ T cells showed a similar, low rate of homeostatic turnover as wild-type naive CD8$^+$ T cells (FIG. 2B). However, all of the comparison stimulation conditions induced varying degrees of cell proliferation.

To assess the transcriptional reprogramming of effector differentiation, transcript abundance for TFs and effector molecules that change during effector differentiation was measured. Key regulators, such as T-bet (Thx21), Eomesodermin (Eomes), and Blimp1 (Prdm1), as well as effector molecules including granzyme A and B, perforin1, and IFNγ, and TNFα were unchanged in GFP$^+$ naive CD8$^+$ T cells relative to wild-type naive CD8$^+$ but were upregulated in stimulation conditions (FIG. 2C). Moreover, immune cell types in blood 8-12 weeks after transplantation into recipient mice (FIG. 2D). Thus, GFP$^+$ naive CD8$^+$ T cells that had developed from transduced LSK cells were indistinguishable from untransduced naive CD8$^+$ T cells, indicating that transduction of LSK cells does not perturb the future development of naive T cells. In contrast, existing protocols to achieve viral transduction of T cells are associated with marked perturbation of the T cell state and partial effector differentiation.

Figure 3:
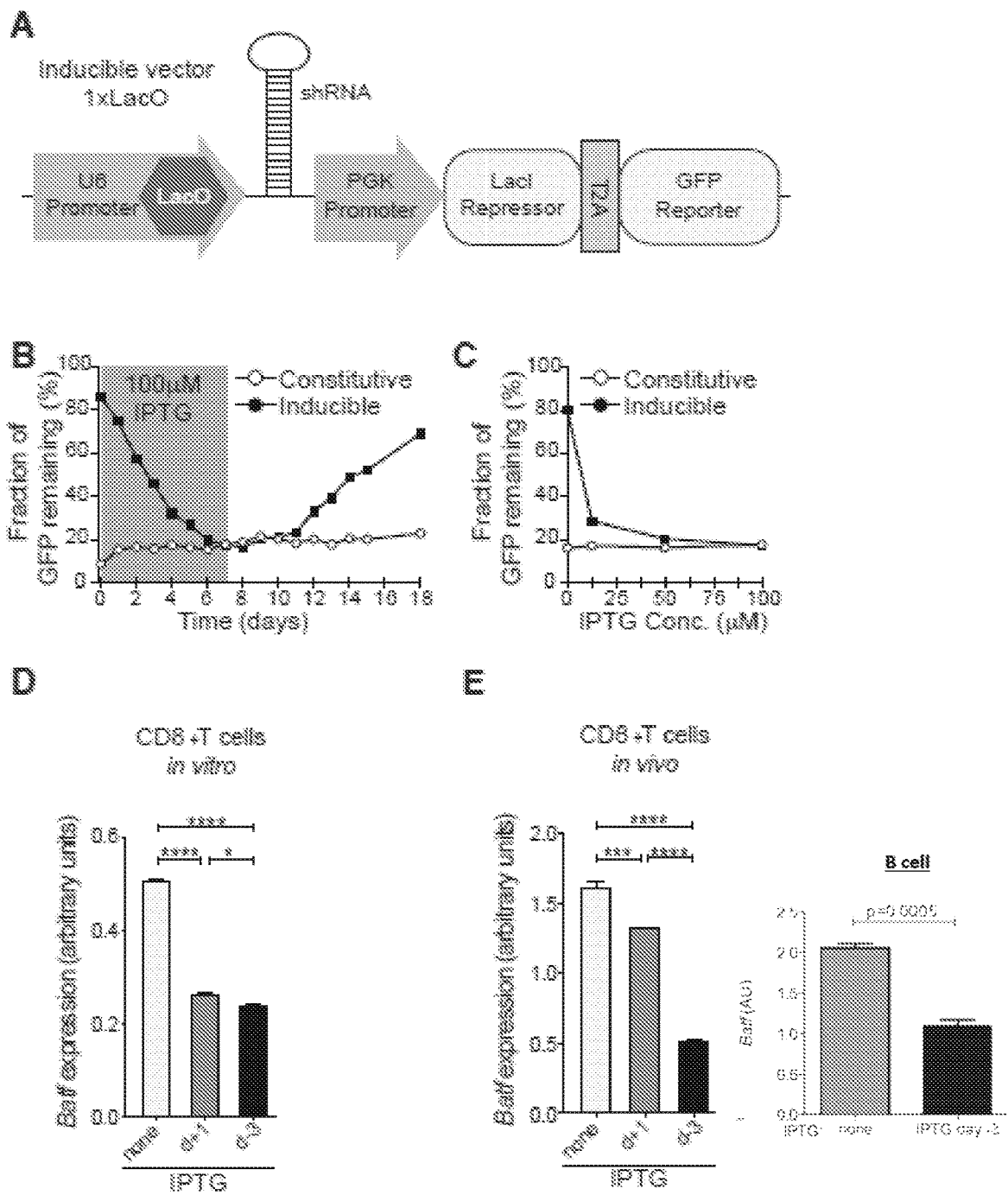
FIG. 3 includes 8 panels, identified as panels A, B, C, D, E, F, G, and H, which show that novel shRNA vectors enable efficient, inducible, and transient gene knockdown in vitro and in vive. Panel A shows a schematic diagram of inducible (1×LacO) vector. The fraction of GFP-expressing Jurkat cells transduced with lentivirus expressing an shRNA targeting GFP under constitutive (white symbols) or inducible (black) promoters, cultured with 100 µM IPTG (grey box) for times indicated (Panel B) or concentrations of IPTG indicated (Panel C) for 7 days are indicated. Panel D shows BATF expression in anti-CD3/CD28-stimulated shBATF-naive CD8$^+$ T cells cultured in vitro with (grey or black bars) or without (white) IPTG starting at the day indicated. Cells were continuously exposed to IPTG by in vivo exposure in BMC mice 3 days prior to T cell sort or to the medium 1 day following activation and for the remainder of the experiment. Panel E shows the results of cells treated as in Panel D or similarly with selected B cells that were transferred in LCMV-infected recipient mice, exposed to IPTG, and maintained by treating mice with 20 mM IPTG in drinking water starting 3 days prior transfer (in BMC) or 1 day following transfer until 3 days following transfer. Batf mRNA level was normalized to Hprt and $2^{-\Delta Ct}$ values reported. Significance was assessed with one-way ANOVA. *P<0.05, *P<0.001, **P<0.0001. Panel F shows a schematic diagram of inducible vector having 3 LacO control elements (3×LacO). Panels G and H show the kinetics of the 1×LacO and 3×LacO vectors as described in Panels B and C.
Figure 3:
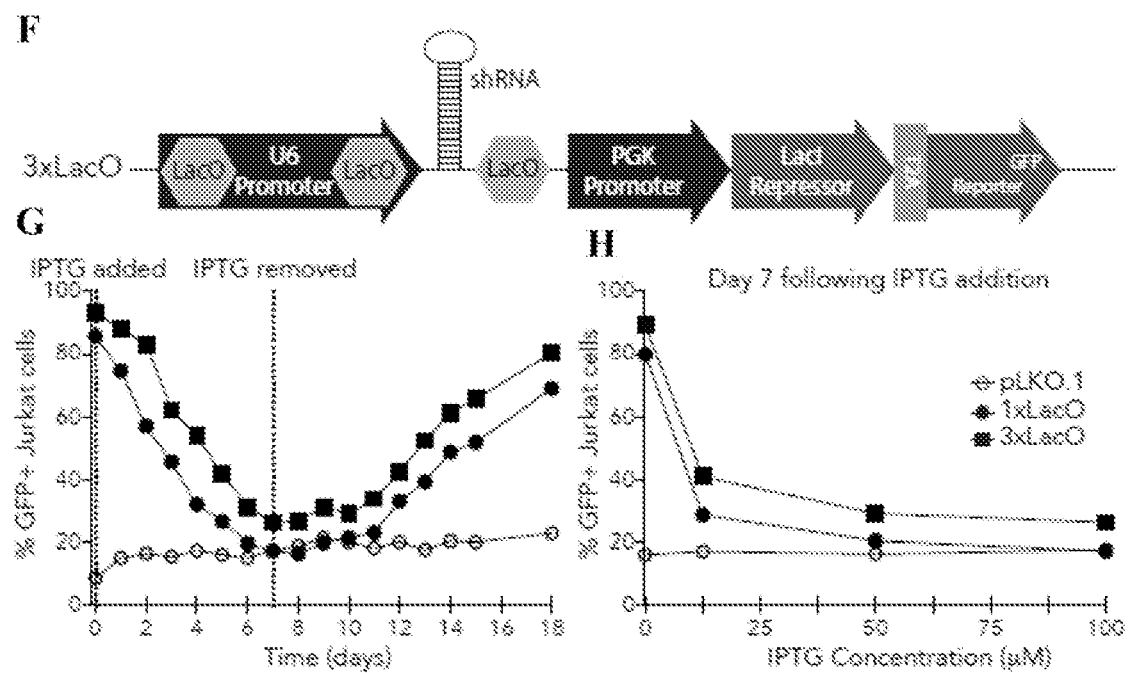

Example 4: Lac Operon-Regulated shRNA Allows Inducible, Efficient, and Transient Gene Knockdown In Vivo at Low Concentrations of IPTG Hematopoiesis depends on the expression of appropriate genes at the proper developmental stage. Because constitutive gene knockdown in LSK could compromise the development of immune lineages, an inducible shRNA expression vector that uses the Lac operon system to regulate the shRNA promoter following addition of isopropyl β-D-1-thiogalactopyranoside (IPTG) was employed (FIG. 3A). This vector provided shRNA inducibility in cancer cell lines in vitro and xenografts in mice. The inducibility of gene knockdown was confirmed by targeting a control gene in a Jurkat cell line. Target gene expression was only minimally affected in the uninduced state (FIGS. 3B-3C). However, gene knockdown following IPTG induction of shRNA expression was as efficient as that achieved by a constitutive shRNA expressing vector (FIG. 3B) even at low concentrations of IPTG (FIG. 3C).

To test knockdown efficiency in primary CD8$^+$ T cells, BMC were generated with an IPTG-inducible vector encoding an shRNA targeting BATF (shBATF) and a GFP expression cassette to create GFP$^+$ naive T cells that carried the inducible shRNA vector (hereinafter, "shBATF-naive T cells"). The knockdown of BATF in GFP$^+$ CD8$^+$ T cells following in vitro activation in the presence or absence of ITPG was assessed (FIG. 3D). Decreased target gene expression was seen as early as 2 days following IPTG addition in vitro (FIG. 3D) and was comparable to knockdown with the constitutive vector. Similarly, a vector containing 3 LacO operators (3×LacO; FIG. 3F) was compared to the 1×LacO vector shown in FIG. 3A and the kinetics of induction and repression are shown in FIGS. 3G-3H.

To test inducible knockdown in vivo, shBATF-naive P14 CD8$^+$ T cells were transferred into LCMV-infected mice and the mice were treated with IPTG. BATF expression was measured after three days. Initiating IPTG induction 1 day following cell activation resulted in modest (18%) gene knockdown, but treating BMC three days prior to transfer resulted in significantly more robust silencing (68% knockdown) 3 days following transfer and infection (FIG. 3E). Similar results were obtained for transferred B cell populations (FIG. 3E). Thus, efficient, inducible gene knockdown was achieved in unperturbed CD8$^+$ T cells.

Figure 4:
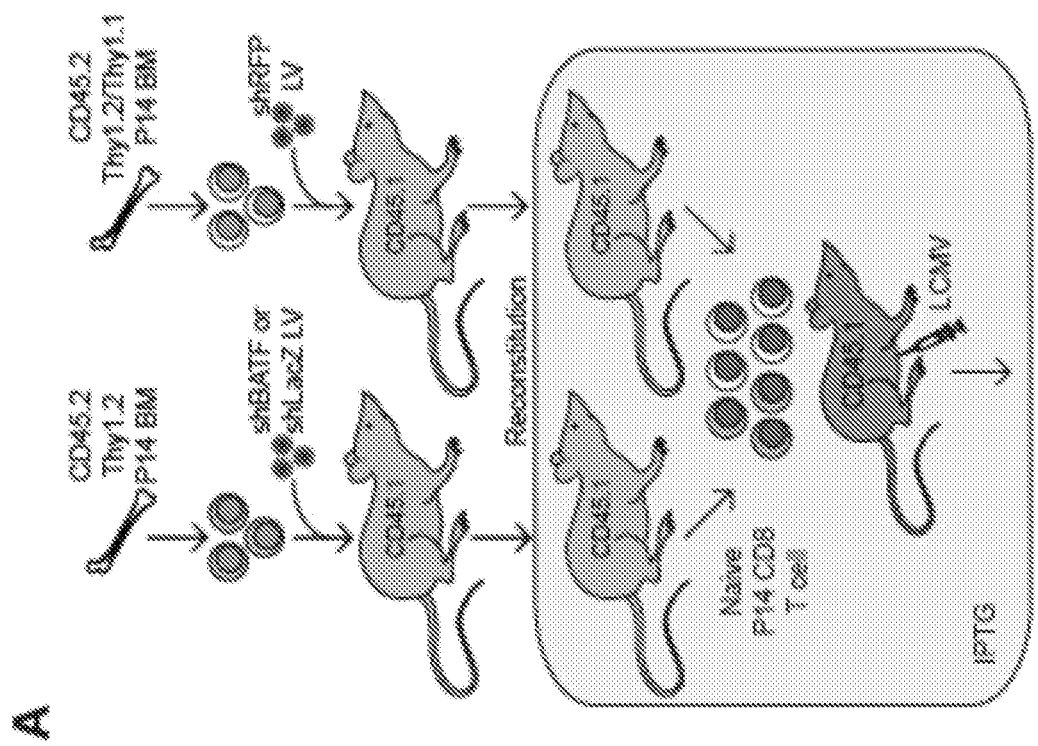
FIG. 4 includes 6 panels, identified as panels A, B, C, D, E, and F, which show that BATF knockdown in vivo in primary CD8$^+$ T cells impairs effector differentiation. Panel A shows a schematic diagram of the experiment. Panel B shows the relative fraction of P14 shBATF- (solid gates/lines) or shRFP- (dotted gates/lines) CD8$^+$ T cells at the time of transfer or at day 7 (d7) p.i. in IPTG-treated animals (from d-3 on). Representative plots (left, middle panel) from a single animal and summary data from 5 mice (right panel) are shown. Panel C shows the ratio of P14 shBATF- or shLacZ-effector CD8$^+$ T cells to shRFP-effector CD8$^+$ T cells at d8 p.i. with IPTG induction. The ratio at d8 p.i. was normalized to the ratio at d0 and results are shown for 3 different shRNAs targeting BATF. Panel D shows proliferation of shBATF- or shLacZ-effector CD8$^+$ T cells measured by BrdU incorporation at d5 p.i. Panels E and F show apoptosis of shBATF- or shLacZ-effector CD8$^+$ T cells measured by active caspase staining (FLICA) at d5 p.i. and Ki67 staining (Panel F). Significance was assessed with Student's t-test; $P<0.01$, **$P<0.0001$.
Figure 4:
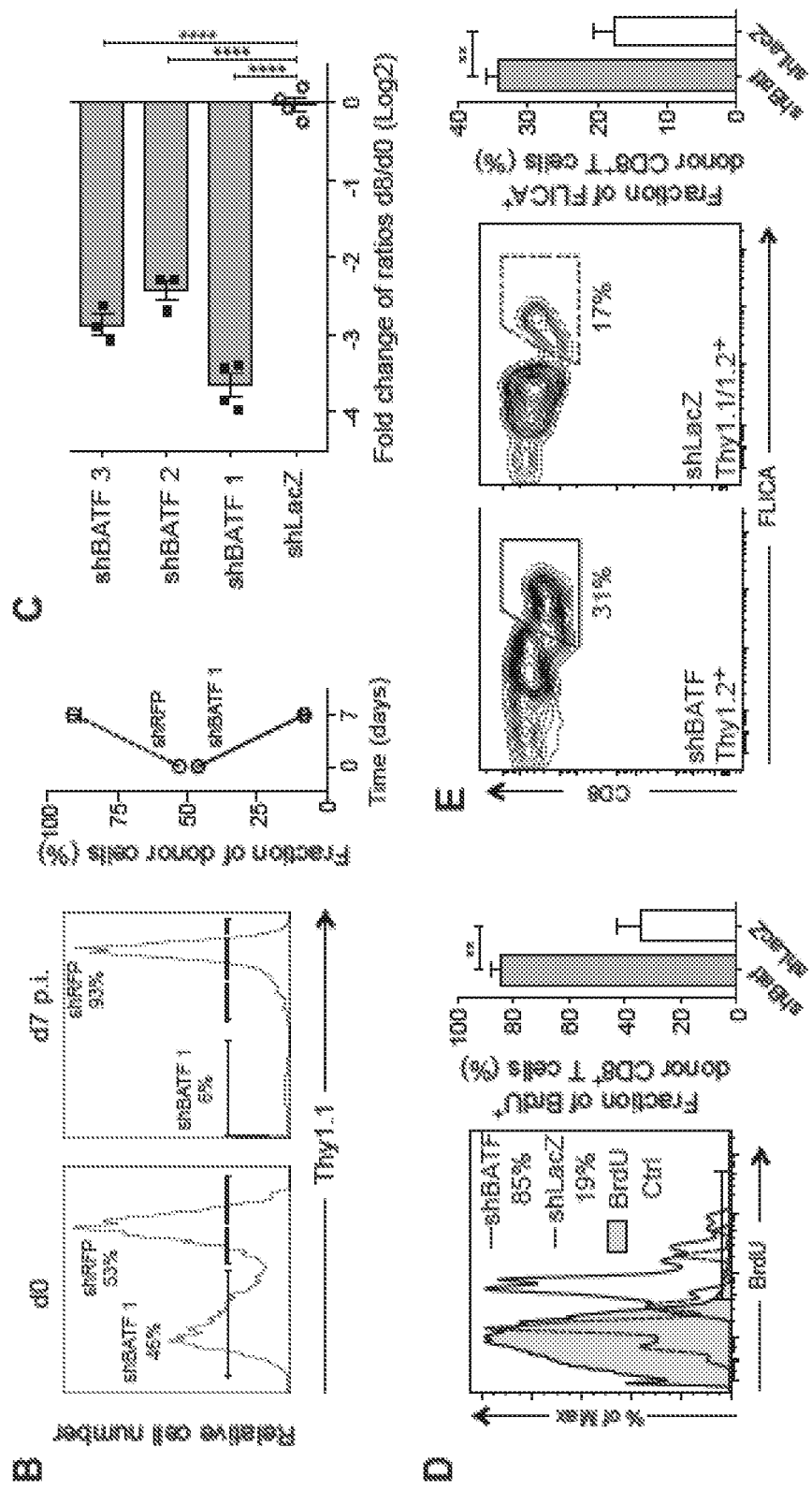
Figure 4:
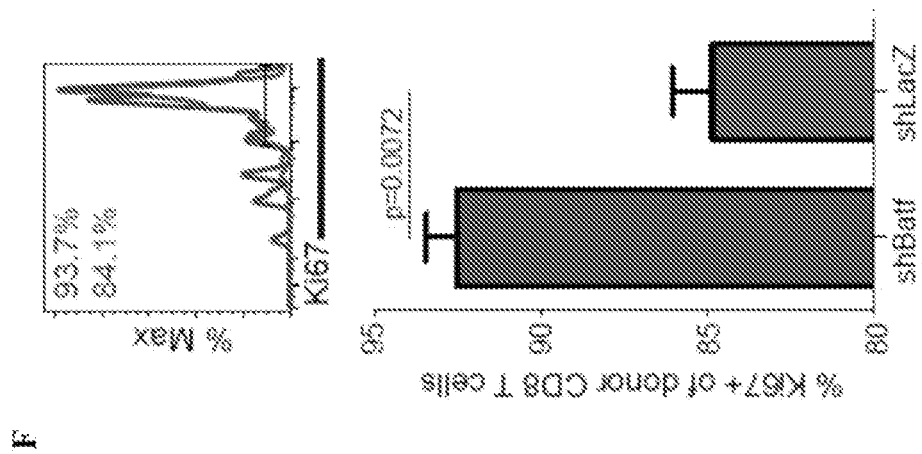

Example 5: BATF Knockdown Impairs CD8$^+$ Effector T Cell Activation and Differentiation Following Acute Viral Infection Batf$^{-/-}$ CD8$^+$ T cells show profoundly impaired effector CD8$^+$ T cell differentiation. To test whether BATF knockdown in wild-type CD8$^+$ T cells also affected effector differentiation, naive P14 CD8$^+$ T cells from BMC transduced with either an inducible shBATF vector or a control shRNA vector targeting LacZ were adoptively transferred into a wild-type recipient in a 1:1 ratio with naive P14 CD8$^+$ T cells from a BMC transduced with a second control shRNA (RFP) (FIG. 4A). Endogenous, shBATF- or shLacZ- and shRFP-naive CD8$^+$ T cells were distinguished by the use of congenic markers. Comparison of the ratio of numbers shBATF- or shLacZ-effector T cells to shRFP-effector T cells was used to analyze the effect of BATF knockdown while controlling for any effect of shRNA expression on differentiation. It was found that P14 shBATF-effector CD8$^+$ T cells showed markedly reduced numbers at day 7-9 post infection (p.i.) relative to shRFP P14 CD8$^+$ T cells. In contrast, the ratio of shLacZ-effectors to shRFP-effectors remained constant (FIGS. 4B-4C). This reduction in shBATF-effector cell numbers was seen with three different BATF shRNAs designed with different seed regions (FIG. 4C) (Jackson et al. (2006) *RNA* 12:1179-1187), indicating that the reduced shBATF-effector cell numbers were unlikely to be due to off-target effects (FIG. 4C). Thus, knockdown of BATF markedly reduces the peak population size of effector CD8$^+$ T cells.

The reduced population size of effector CD8$^+$ T cells following BATF knockdown could be due to altered T cell expansion or increased cell death. To identify the mechanism of impaired effector differentiation, proliferation (by BrdU incorporation) and cell death (by the abundance of activated caspases) were both measured in shBATF-effector CD8$^+$ T cells at day 5 p.i. Despite the decrease in effector cell numbers seen at day 8 p.i., a significantly larger fraction of remaining shBATF-effector CD8$^+$ T cells were proliferating than shLacz-effector CD8$^+$ T cells (FIG. 4D). However, simultaneous analysis of active caspase abundance showed significantly higher apoptosis in shBATF-effector CD8$^+$ T cells (FIG. 4E). In addition, cell division, as measured by Ki67 expression, was also increased in shBATF-effector CD8$^+$ T cells (FIG. 4F). Thus, knockdown of BATF caused both increased proliferation and increased cell death in early effector differentiation.

Example 6: BATF is Required to Initiate but not Maintain Effector CD8$^+$ T Cell Differentiation Previous studies have demonstrated that BATF is required to initiate effector differentiation, as naive Batf$^{-/-}$ T cells undergo massive cell death at 72-96 hrs. after stimulation (Kurachi et al. (2014) *Nat. Immunol.* 15:373-383). However, because previous studies of the role of BATF in effector CD8$^+$ differentiation have been carried out using constitutive germline deletions, it is not known whether BATF is required only to initiate effector differentiation (i.e., at the time of initial antigen encounter), or whether it is also needed to maintain effector differentiation once underway. Because the inducible shRNA system allows temporal control of BATF knockdown, whether delayed BATF knockdown impaired effector differentiation to the same extent as knockdown at the time of infection was tested.

Figure 5:
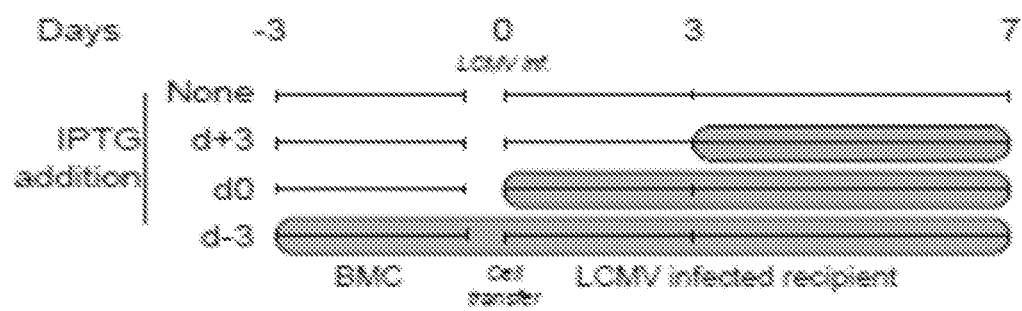
FIG. 5 includes 2 panels, identified as panels A and B, which show that BATF is required to initiate but not maintain effector differentiation. Panel A shows a schematic diagram of timing of IPTG induction. Panel B shows the ratio of shBATF- or shLacZ-effector CD8$^+$ T cells to shRFP-effector CD8$^+$ T cells at d8 p.i. with continuous IPTG induction initiated for the times indicated. Day 8 p.i. ratios were normalized to the d0 ratio and were Log 2 transformed. Significance was assessed with one-way ANOVA. $P<0.01$, *$P<0.001$, ****$P<0.0001$.
Figure 5:
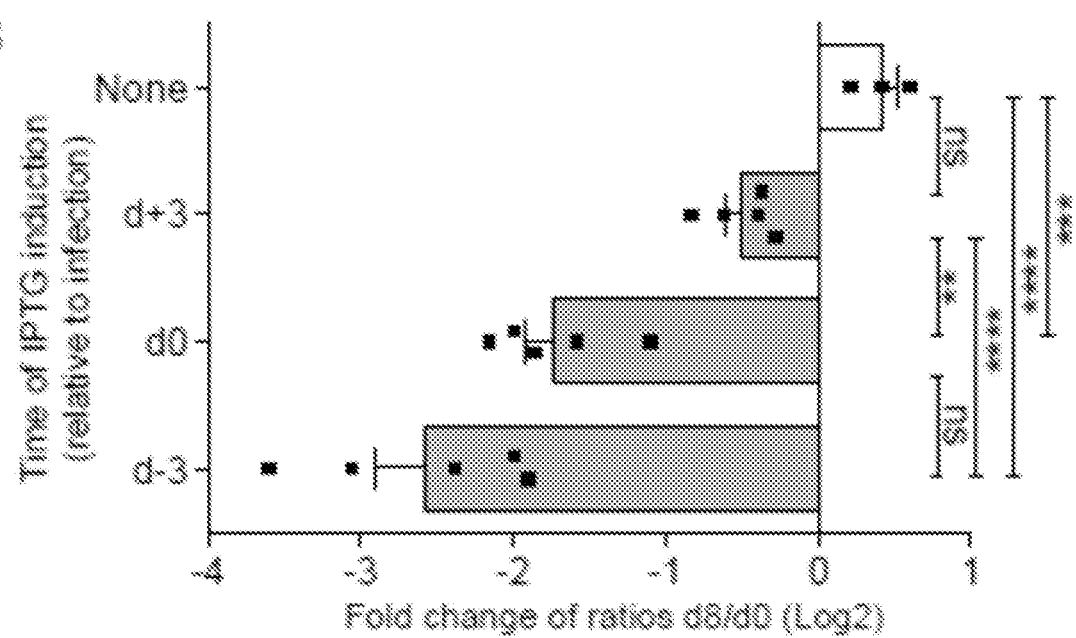

To address this question, a 1:1 mixtures of congenically distinguishable P14 shBATF- or shLacZ-CD8$^+$ T cells were adoptively transferred into recipient wild-type animals, which were then infected with LCMV-Armstrong. IPTG was administered to induce BATF knockdown either before infection, at the time of infection, or 72 hr. p.i (FIG. 5A). Comparison of the relative frequency of shBATF-effector cells to shLacZ-effector cells at day 8 p.i. showed that inducing BATF knockdown 3 days prior to infection or at the time of infection was associated with a significant reduction in the numbers of effector $CD8^+$ T cells compared to controls with no IPTG induction. However, inducing BATF knockdown 72 hrs. post-infection did not significantly change effector expansion (FIG. 5B). Thus, while BATF is required for effector $CD8^+$ T cell differentiation at the time of initial antigen encounter, by 72 hrs. p.i., BATF becomes largely dispensable at least through day 8 of effector differentiation. This indicates that BATF is required to initiate but not maintain transcriptional reprogramming of effector $CD8^+$ T cells.

Figure 6:
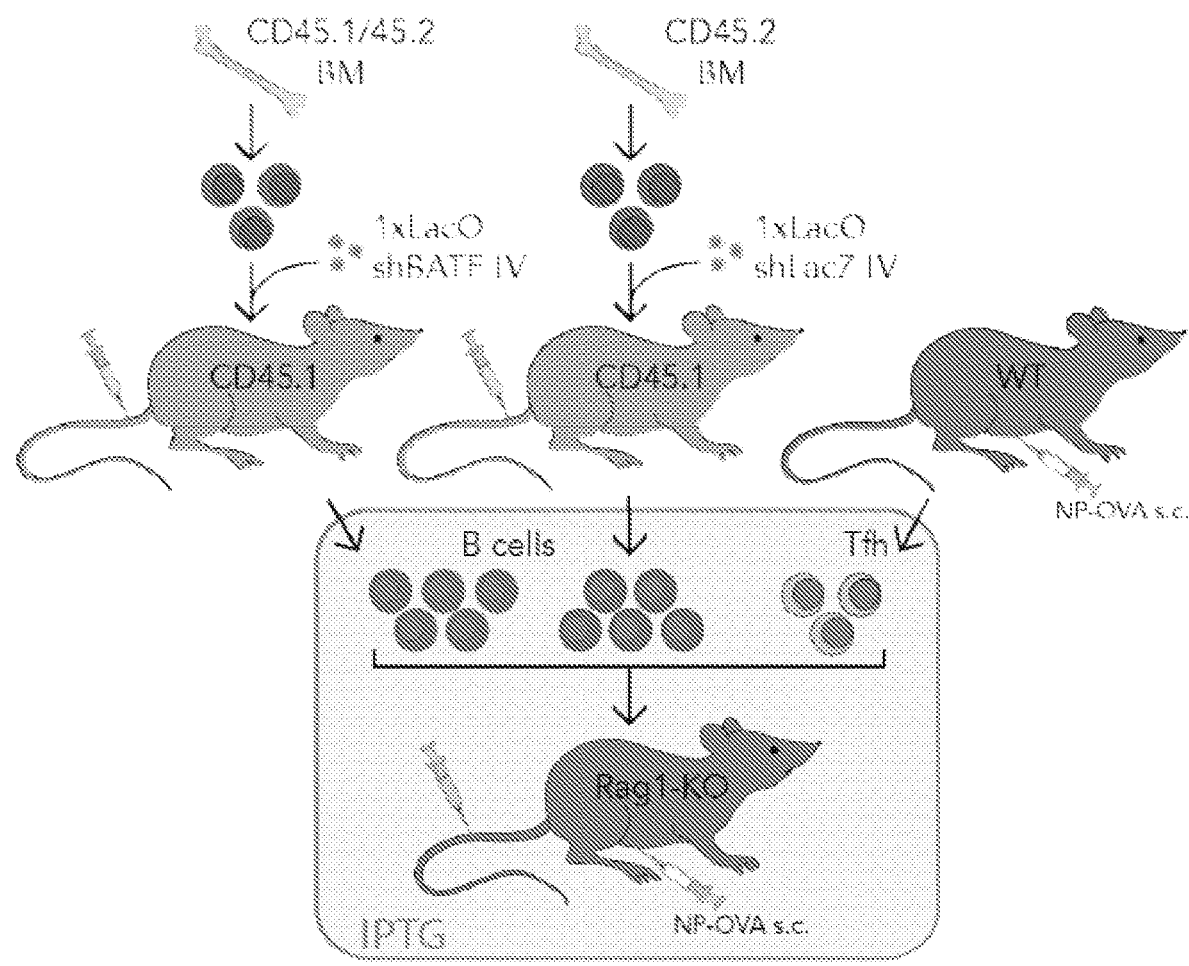
FIG. 6 includes 3 panels, identified as panels A, B, and C, which show that BATF knockdown (Panel A) results in defective activation and differentiation of B cells (Panel B), as well as defects in plasma cell differentiation (Panel C).
Figure 6:
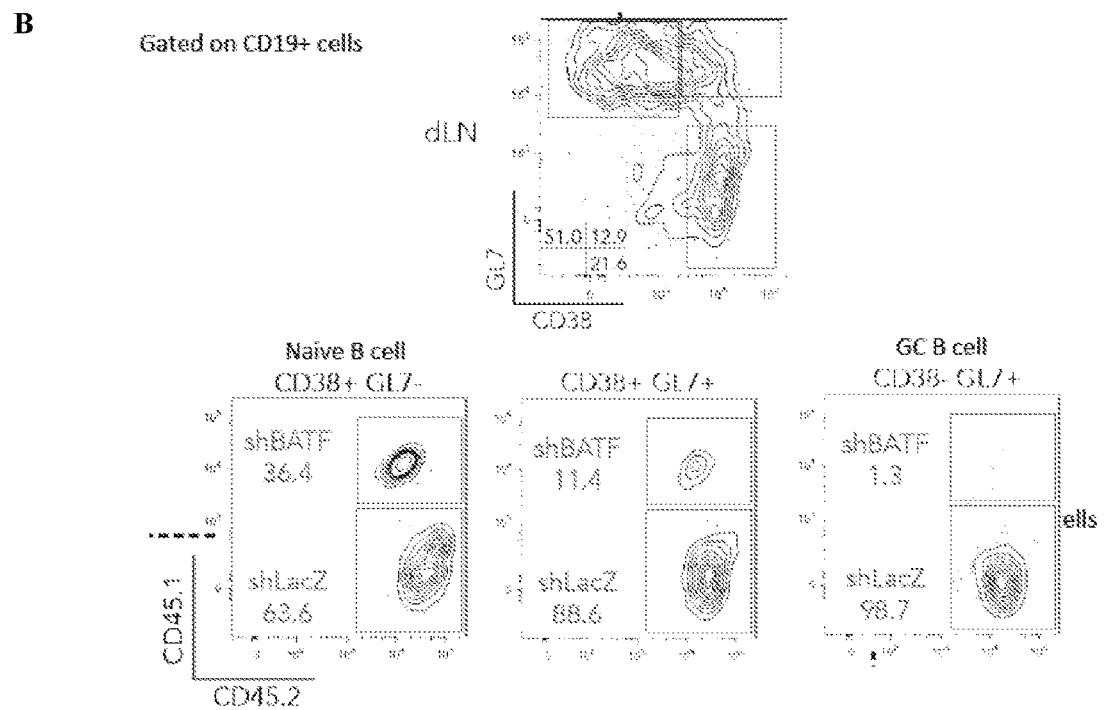
Figure 6:
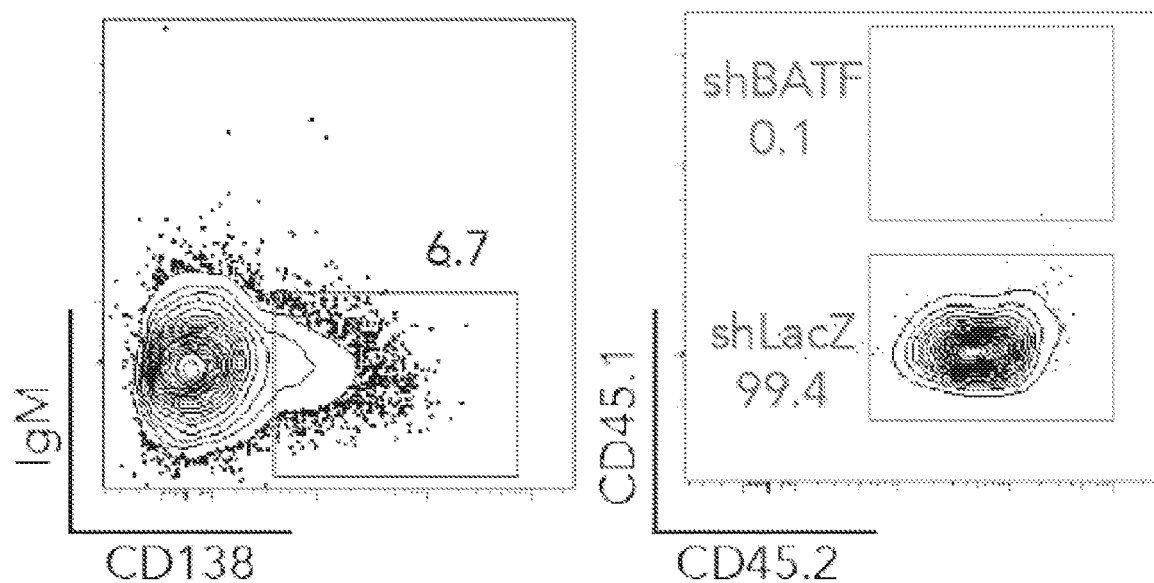

Example 7: BATF Knockdown Results in Defected Activation and Differentiation of B Cells Naive B cells from BMC transduced with either an inducible shBATF vector or a control shRNA vector targeting LacZ were adoptively transferred into recipients shown in FIG. 6A in order to determine the role of BATF in B cell activation and differentiation. BATF knockdown resulted in defective activation and differentiation of B cells (FIG. 6B), as well as defects in plasma cell differentiation (FIG. 6C).

Thus, a strategy to inducibly silence gene expression in unperturbed hematopoietic cells in vivo using RNAi has been determined. This system was used to show that BATF is required to initiate effector $CD8^+$ T cell differentiation, but becomes dispensable after 72 hrs. The findings indicate that the experimental approach can accelerate the analysis of gene function in early cell fate commitment in the hematopoietic system.

The ability to manipulate gene expression using RNAi has proven a powerful tool with which to investigate gene function in the immune system. Silencing gene expression in T cells (Joshi et al. (2007) *Immunity* 27:281-295; Araki et al. (2009) *Nature* 460:108-112; Zhou et al. (2014) *Nature* 506:52-57) or dendritic cells (Amit et al. (2009) *Science* 326:257-263; Chevrier et al. (2011) *Cell* 147:853-867) has allowed the rapid identification of regulators of cell differentiation and activation. Viral vectors expressing shRNA molecules are the most frequently used delivery method for RNAi. However, this approach is limited by the inability to deliver viral vectors to quiescent T cells. As a result, most approaches have used activation in vitro (Yang et al. (2012) *J. Exp. Med.* 209:1655-1670; Zhou et al. (2014) *Nature* 506:52-57) or in vivo (Joshi et al. (2007) *Immunity* 27:281-295; Araki et al. (2009) *Nature* 460:108-112) to achieve efficient transduction. However, both of these approaches profoundly alters the underlying transcriptional and functional state of naive T cells. T cells activated in vitro, even in the absence of TCR stimulation, show upregulation of TFs and cytotoxic molecules including granzymes, indicating that many aspects of effector differentiation are initiated by these manipulations even before viral infection and gene knockdown can occur. In contrast, the experimental system described herein permits the inducible knockdown of genes in quiescent, unperturbed naive T cells, allowing the events that occur during the minutes to hours after T cell stimulation to be interrogated. Thus, this approach now allows functional genomic studies in transduction-refractory cells in vive without ex vivo perturbation.

The system was used to analyze the role of BATF in the immediate hours after antigen encounter. BATF plays a profound role in the differentiation of many cell lineages of the immune system (Murphy et al. (2013) *Nat. Rev. Immunol.* 13:499-509). It is required for the development of $T_{FH}$ (Chevrier et al. (2011) *Cell* 147:853-867) and Th17 (Schraml et al. (2009) *Nature* 460:405-409; Ciofani et al. (2012) *Cell* 151:289-303) cells and for class switching in B cells (Chevrier et al. (2011) *Cell* 147:853-867), indicating it plays an essential role in cell differentiation in diverse lineages. Recent studies in $CD8^+$ T cells show that loss of BATF dysregulates a suite of TFs, cytokine sensors, and metabolic pathways leading to a profound defect in effector $CD8^+$ T cell differentiation (Kurachi et al. (2014) *Nat. Immunol.* 15:373-383). However, while these studies show that BATF is required to initiate effector $CD8^+$ differentiation, it remains unclear whether BATF is also needed to maintain the differentiation program once underway. It has been shown herein that BATF is required at or immediately after antigen encounter, but rapidly becomes dispensable for subsequent development of effector $CD8^+$ T cells until at least d8 p.i. These results indicate that BATF is required to initiate but not maintain the effector differentiation program.

These findings are consistent with several prior observations that support a role for BATF in the initial commitment to an effector state. First, the defects in effector $CD8^+$ T cells that lack BATF are evident within 72-96 hrs. of antigen encounter (Kurachi et al. (2014) *Nat. Immunol.* 15:373-383), indicating that BATF plays a critical function in the earliest hours of effector differentiation. Second, BATF associates with its binding sites within 24 hours of T cell activation, which indicates that it could play a regulatory role as early as hours after antigen encounter (Kurachi et al. (2014) *Nat. Immunol.* 15:373-383). Finally, during Th17 differentiation, loss of BATF results in decreased chromatin accessibility at some regions normally bound by BATF, which indicates that BATF may play a role as a pioneer TF (Ciofani et al. (2012) *Cell* 151:289-303). Pioneer TFs can regulate the chromatin structure at critical regulatory regions to enable the subsequent binding of other TFs (Magnani et al. (2011) *Trends Genet.* 27:465-474). The findings of a transient role for BATF at the initiation of effector differentiation described herein are consistent with its function as pioneer TF. For instance, BATF may function at the start of effector $CD8^+$ differentiation to increase chromatin accessibility to other effector TFs that cement the differentiation state. Because BATF is no longer required for effector differentiation by 72 hrs., other TFs, such as T-bet and STAT proteins, may be responsible for maintaining effector differentiation once underway (Vahedi et al. (2012) *Cell* 151:981-993). Analysis of the temporal role of candidate effector TFs, either with the inducible RNAi system, or with conditional knockout strains can be used.

Previous studies of BATF in $CD8^+$ differentiation showed that $Batf^{-/-}$ but not $Batf^{+/-}$ T cells displayed a defect in effector differentiation suggesting that the remaining expression in $Batf^{+/-}$ is sufficient for proper T cell activation (Kurachi et al. (2014) *Nat. Immunol.* 15:373-383). In this context, it is perhaps surprising that 68% knockdown of BATF (FIG. 3E) was associated with such marked impairment of effector differentiation white the BATF heterozygous mouse was not. Alternatively, compensatory mechanisms or adaptation may be in effect when the cells are lacking half of genomic BATF throughout their development. It is believed that there may be a critical "dose" of BATF that is required for normal effector $CD8^+$ T cell differentiation: knockdown of BATF reduces protein abundance below this threshold while heterozygous deletion does not.

These findings help provide a mechanism to explain why effector differentiation can be initiated by brief, transient TCR activation. Studies of temporally-limited antigen-exposure have shown that as little as 4 h of TCR stimulation can initiate cell division and induce cytolytic function in naive CD8$^+$ T cells (van Stipdonk et al. (2001) *Nat. Immunol.* 2:423-429), and only 20 hrs. of stimulation can initiate a self-sustaining program of effector and memory differentiation that is cell autonomous (Kaech and Ahmed (2001) *Nat. Immunol.* 2:415-422; van Stipdonk et al. (2003) *Nat. Immunol.* 4:361-365). Although the ultimate fate of effector cells is strongly modulated by antigen persistence, inflammation and the cytokine milieu, these studies indicate that CD8$^+$ T cells encounter an irreversible decision point within hours of antigen encounter (Kaech and Ahmed (2001) *Nat. Immunol.* 2:415-422). The findings described herein indicate that transcriptional regulation by BATF may be one component of that decision point. BATF may launch differentiation by irreversibly engaging the effector transcriptional program within the first 24 hrs. of stimulation.

The use of a bone marrow chimeric system results in transduction of all hematopoietic-derived lineages with the inducible shRNA vector. As such, analysis of gene function in other cell types that are refractory to viral transduction, such as naive CD4$^+$ T cells or B cells, is now equally feasible. The use of this strategy should provide a broadly useful tool for interrogating gene function within unperturbed cells of hematopoietic origin.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of generating transduced resting cells of the hematopoietic stem cell lineage that are differentiated in vivo and inducibly express an RNA encoded by an exogenous DNA integrated into the genome of the cells by at least one viral vector, comprising:
   a) obtaining cells of the hematopoietic stem cell lineage;
   b) transducing the cells with at least one viral vector, wherein each viral vector integrates an exogenous DNA into the genome of the cell and the integrated exogenous DNA inducibly expresses an RNA encoded by the exogenous DNA; bb
   c) transplanting the transduced cells to an immunocompromised incubator animal, wherein the transplanted transduced cells reconstitute the immunocompromised incubator animal immune system;
   d) selecting populations of resting reconstituted immune cells of interest from the incubator animal; and
   e) transplanting the resting reconstituted immune cells of interest from the incubator animal transduced resting cells of the hematopoietic stem cell lineage that are differentiated in vivo into an experimental animal, wherein the experimental animal expresses an inducer of the inducible RNA expression before transplantation, and monitoring the transplanted cells in response to exogenous perturbation,
   thereby generating transduced resting cells of the hematopoietic stem cell lineage that are differentiated in vivo and inducibly express an RNA encoded by an exogenous DNA integrated into the genome of the cells by at least one viral vector.

2. The method of claim 1, wherein the cells of the hematopoietic stem cell lineage are murine or human.

3. The method of claim 1, wherein the cells of the hematopoietic stem cell lineage are selected from the group consisting of hematopoietic stem cells (HSC), common myeloid progenitor cells (CMP), common lymphoid progenitor cells (CLP), committed lymphoid progenitor cells, granulocyte/macrophage progenitor cells (GMP), megakaryocyte/erythroid progenitor cells (MEP), granulocyte progenitor cells, macrophage progenitor cells, erythroid progenitor cells, megakaryocyte progenitor cells (MKP), NK cell progenitor cells (NKP), B cell progenitor cells (BCP), and T cell progenitor cells (TCP), optionbally wherein the cells of the hematopoietic stem cell lineage
   i) are not terminally differentiated or post-mitotic;
   ii) are not thymocytes or are not derived from the thymus; and/or
   iii) are obtained from a biological source selected from the group consisting of bone marrow, umbilical cord blood, amniotic fluid, peripheral blood, and fetal liver.

4. The method of claim 1, wherein the cells are transduced with a single viral vector.

5. The method of claim 1, wherein the viral vector is a lentiviral vector.

6. The method of claim 1, wherein the inducible expression is regulated using lactose operon operator (LacO) and lactose operon repressor (LacI) sequences.

7. The method of claim 1, wherein the RNA
   i) is selected from the group consisting of mRNA, antisense RNA, shRNA, siRNA, microRNA, PiwiRNA, and combinations thereof;
   ii) is an shRNA; and/or
   iii) is an engineered, non-naturally occurring Clustered Regularly Interspaced Short Palindromic Repeats (CRISPR) guide RNA that hybridizes with a target nucleic acid sequence of interest.

8. The method of claim 1, wherein the viral vector further comprises a nucleic acid encoding a reporter or a nucleotide sequence encoding a Type II Cas9 protein.

9. The method of claim 8, wherein the reporter is a fluorescent protein.

10. The method of claim 1, wherein the incubator animal
    i) is immunocompromised using lethal irradiation or chemotherapy; and/or
    ii) is immunodeficient.

11. The method of claim 1, wherein the immunocompromised incubator animal and the animal from which the cells of step a) were obtained are congenic.

12. The method of claim 1, wherein transplantation of the transduced cells to the immunocompromised incubator animal is autologous, syngeneic, allogeneic, or xenogeneic.

13. The method of claim 1, wherein the resting reconstituted immune cells of interest selected in step d)
  i) are selected from the group consisting of terminally differentiated cells, post-mitotic cells, and/or unactivated cells;
  ii) have not been exogenously stimulated to divide;
  iii) are resting T cells or resting B cells; and/or
  iv) are isolated.

14. The method of claim 1, further comprising a step f) of culturing the selected cells in vitro and monitoring the selected cells in response to exogenous perturbation.

15. The method of claim 14, wherein the exogenous perturbation is the application of an assay for testing autoimmune, allergic, vaccination, immunotolerance, cancer immunotherapy, immune exhaustion, immunological memory, immunological epitope, stem cell, hematopoietic stem cell, or immune disease responses.

16. Exogenously perturbed transduced resting cells of the hematopoietic stem cell lineage that are differentiated in vivo produced according to claim 1.

17. Non-human animals comprising exogenously perturbed transduced resting cells of the hematopoietic stem cell lineage that are differentiated in vivo produced according to claim 1.

18. The method of claim 1, wherein the exogenous perturbation is the application of an assay for testing autoimmune, allergic, vaccination, immunotolerance, cancer immunotherapy, immune exhaustion, immunological memory, immunological epitope, stem cell, hematopoietic stem cell, or immune disease responses.

* * * * *

UNITED STATES PATENT AND TRADEMARK OFFICE
CERTIFICATE OF CORRECTION

Page 1 of 1

PATENT NO. : 10,653,123 B2
APPLICATION NO. : 15/314251
DATED : May 19, 2020
INVENTOR(S) : William N. Haining et al.

It is certified that error appears in the above-identified patent and that said Letters Patent is hereby corrected as shown below:

In the Specification

At Column 1, Line 16, please delete:
"This invention was made with government support under grant numbers ROI A1091493, AI057266, and AI082630 awarded by the National Institutes of Health. The government has certain rights in the invention."

And replace with:
-- This invention was made with government support under AI091493, AI057266, and AI082630 awarded by the National Institutes of Health. The government has certain rights in the invention. --

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*